United States Patent [19]
Thorpe et al.

[11] Patent Number: 5,165,923
[45] Date of Patent: Nov. 24, 1992

[54] METHODS AND COMPOSITIONS FOR THE TREATMENT OF HODGKIN'S DISEASE

[75] Inventors: Philip Thorpe, Ruislip; Andreas Engert, London, both of United Kingdom

[73] Assignee: Imperial Cancer Research Technology, London, United Kingdom

[21] Appl. No.: 440,050

[22] Filed: Nov. 20, 1989

[51] Int. Cl.⁵ .................... A61K 39/44; C07K 17/02; C07K 15/28

[52] U.S. Cl. .......................... 424/85.91; 530/391.9; 530/388.7; 530/388.73; 530/388.75

[58] Field of Search ................... 530/390, 391, 388; 424/85.91

[56]  References Cited
FOREIGN PATENT DOCUMENTS
0222360 5/1987 European Pat. Off.

OTHER PUBLICATIONS

Engert et al. (1990a) Cancer Res. 50: 84-88.
Engert et al. (1990b) Cancer Res. 50: 2929-2935.
Fulton et al. (1988a) Cancer Res. 48(9): 2618-25.
Fulton et al. (1988b) Cancer Res. 48: 2626-31.
Ghetia (1988) Cancer Res. 48(9): 2610-17.
Thorpe et al. (1987) Cancer Res. 47: 5924-31.
Thorpe et al. (1988) Cancer Res. 48: 6396-6403.
Hsu et al., "Identification of an M,70,000 Antigen Asssociated with Reed-Sternberg Cells and Interdigitating Reticulum Cells," Cancer Research, 50: 1-8, (1990).
Schwarting et al., "BER-H2: A New Anti-K-1 (CD30) Monoclonal Antibody Directed at Formol-Resistant Epitope," Blood, 74(5): 1678-1689, (1989).
Gause et al., "Soluble Hodgkin-Associated CD30 Antigen Is a Specific Serum Tumor Marker in Hodkgin's Disease: Correlation with Soluble IL-2-Receptor Levels," Blut, 59, 3, 211A, 297 (1989).
Engert et al., "Immunotoxins for the Treatment of Hodgkin's Disease", Blut, 59, 3, 212A, 297 (1989).
Pfreundschuh et al., "Hodkgin and Reed-Sternberg Cell Associated Monoclonal Antibodies HRS-1 and HRS-2 React with Activated Cells of Lymphoid and Monocytoid Origin," Anticancer Research, 8: 217-224, (1988).
Vitetta et al., "Redesigning Nature's Poisons to Create Anti-Tumor Reagents," Science, 238: 1098-1104 (1987).
Hsu et al., "Effect of Monoclonal Antibodies Anti-2H9, Anti-IRac, and Anti-HeFi-1 on the Surface of Antigens of Reed-Sternberg Cells,: JNCI 79(5)", 1091-1099, (1987).
Kronke et al., "Adult T Cell Leukemia: A Potential Target for Ricin A Chain Immunotoxins," Blood, 65(6):1416-1421, (1985).
Stein et al., "The Expression of the Hodgkin's Disease (List continued on next page.)

Primary Examiner—Christine Nucker
Assistant Examiner—Kay K. Kim
Attorney, Agent, or Firm—Arnold, White & Durkee

[57] ABSTRACT

Disclosed are methods and compositions for the treatment of Hodgkin's disease and processes involving Hodgkin's disease cells or Reed-Sternberg cells, through specific elimination of Hodgkin's disease cells through the application of immunotoxin technology. The compositions of the invention include toxin conjugates composed of a Hodgkin's disease cell binding ligand conjugated to a toxin A chain moiety such as ricin A chain or deglycosylated ricin A chain, by means of a cross-linker or other conjugation which includes a disulfide bond. In preferred aspects of the invention, therapeutic amounts of conjugates composed of a CD-30 or IRac antibody or fragment thereof conjugated to deglycosylated A chain by means of an SMPT linker is administered to a Hodgkin's disease patient so as to specifically eliminate Hodgkin's disease cells without exerting significant toxicity against non-tumor cells. Also disclosed are particular hybridomas and monoclonal antibodies, and associated methodology, which may be employed, e.g., in the preparation of these immunotoxins as well as other uses such as diagnostic applications.

29 Claims, 5 Drawing Sheets

OTHER PUBLICATIONS

Associated Antigen Ki-1 Reactive and Neoplastic Lymphoid Tissue: Evidence that Reed-Sternberg Cells and Histiocytic Malignancies are Derived from Activated Lymphoid Cells," Blood, 66(4):848–858, (1985).

Depper et al., "Augmented T Cell Growth Factor Receptor Expression in HTLV-1 Infected Human Leukemic T Cells," The Journal of Immunology 133(4):1691–1695, (1984).

Schwab et al., "Production of a Monoclonal Antibody Specific for Hodgkin and Sternberg-Reed Cells of Hodgkin's Disease and a Subset of Normal Lymphoid Cells," Nature, 299: 65–67, (1982).

Schwarting et al., Leucocyte typing, 3: 574–575, 1987.
Diehl et al., Cancer Surveys, 4(2):399–419, 1985.
Bjorn et al., Cancer Research, 45:1214–1221, 1985.
Press et al., J. Immunol., 141:4410–4417, 1988.
May et al., The J. Immunol., 144:3637–42, 1990.

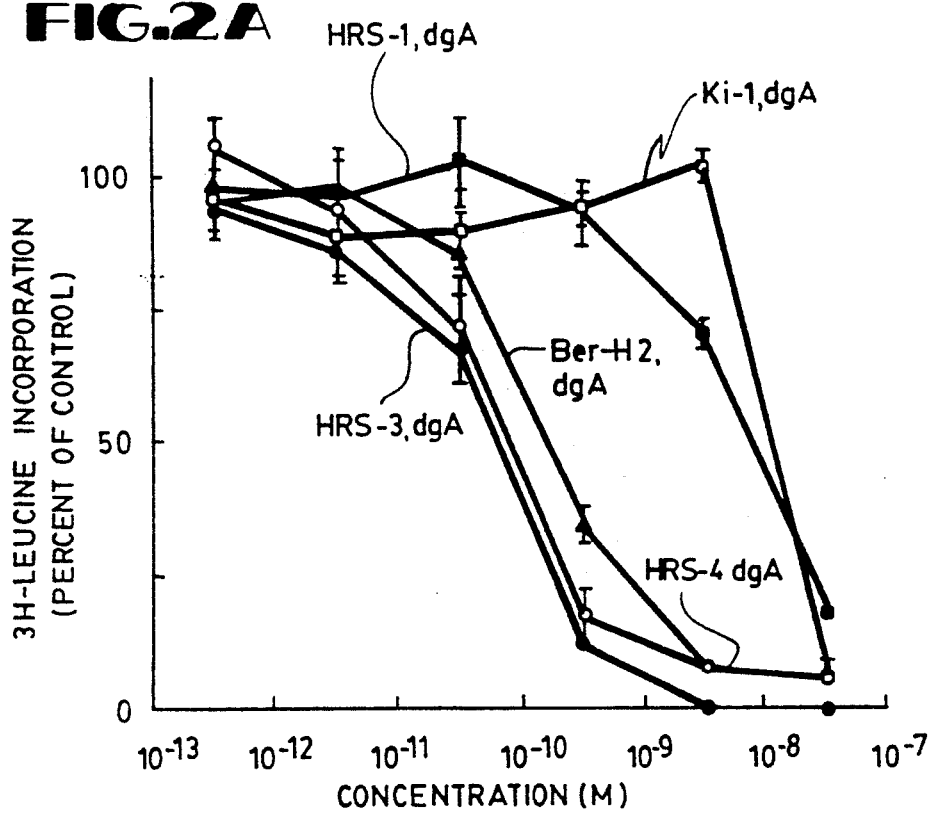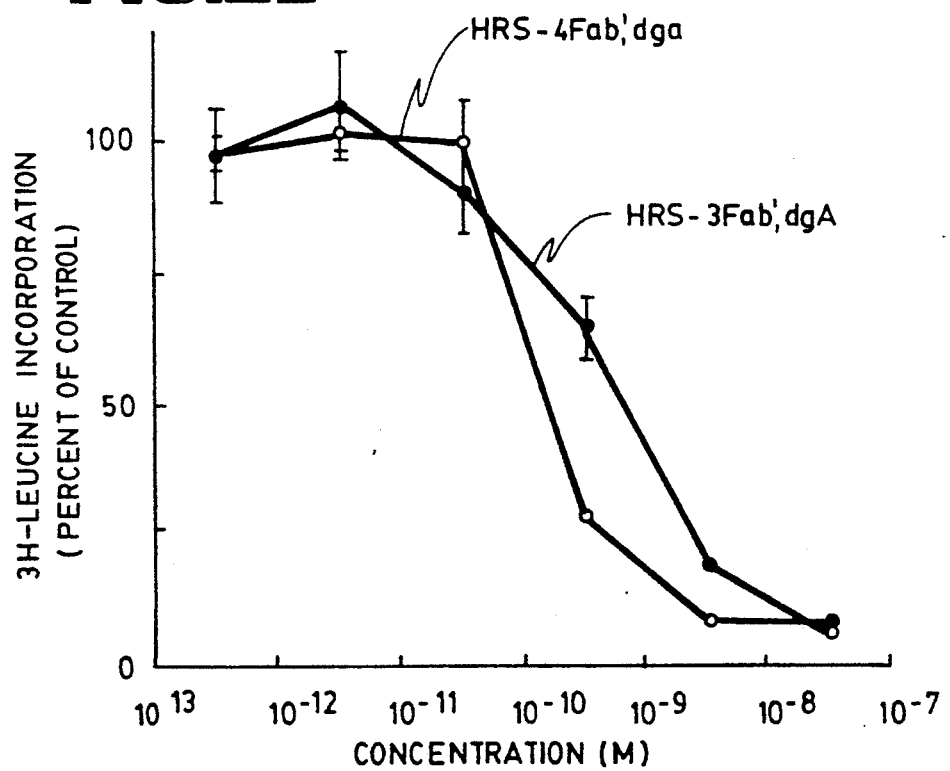

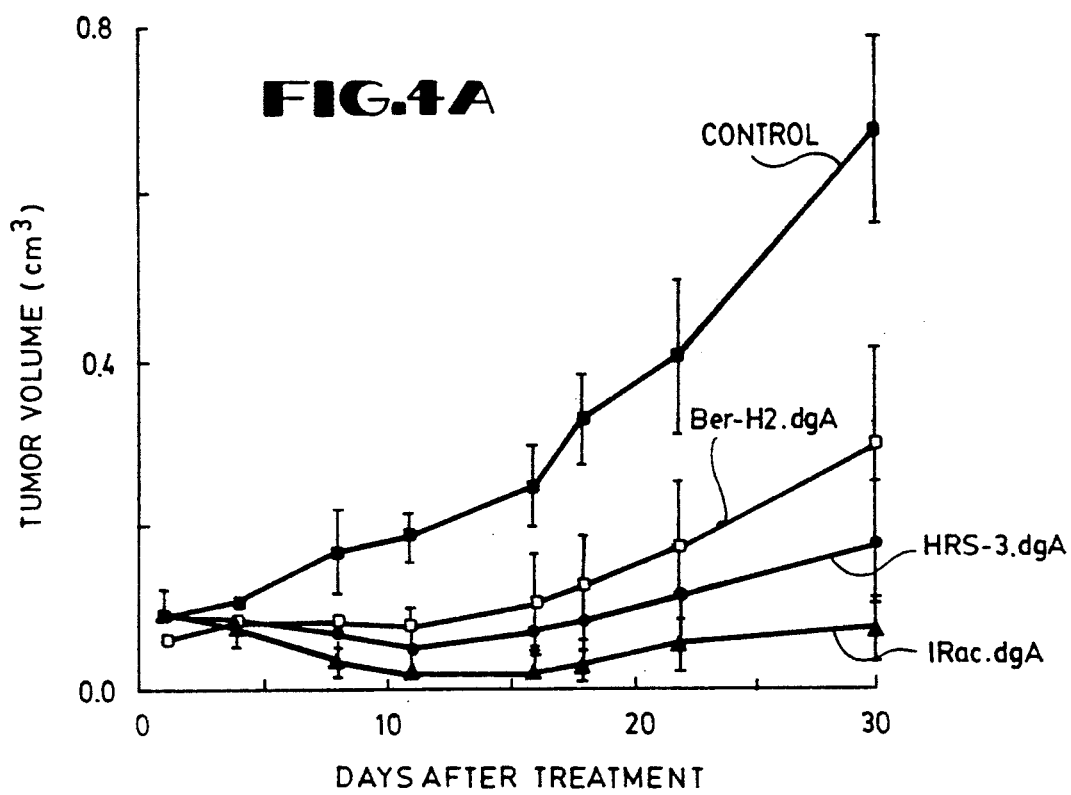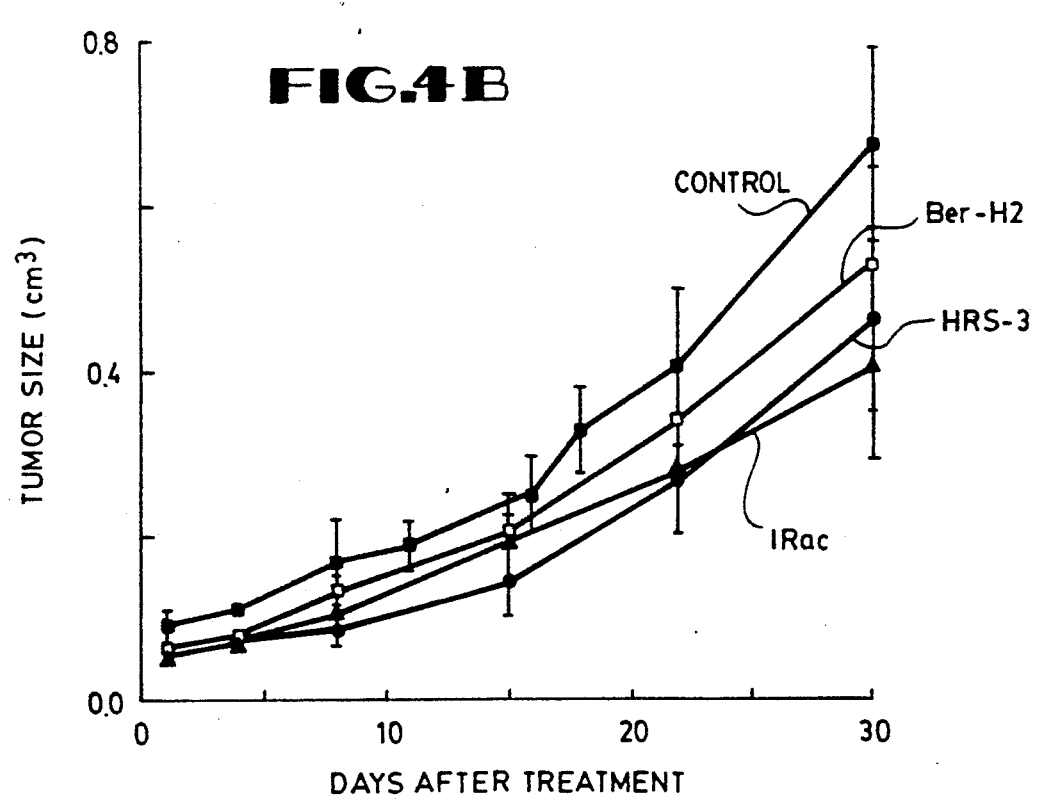

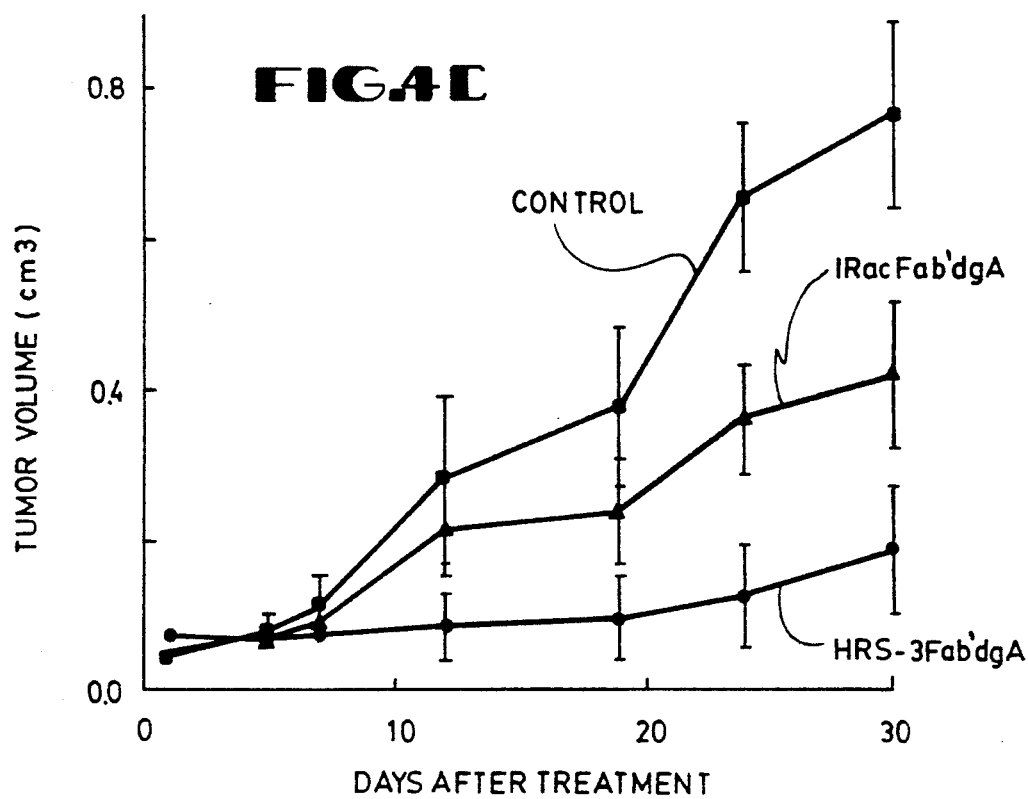
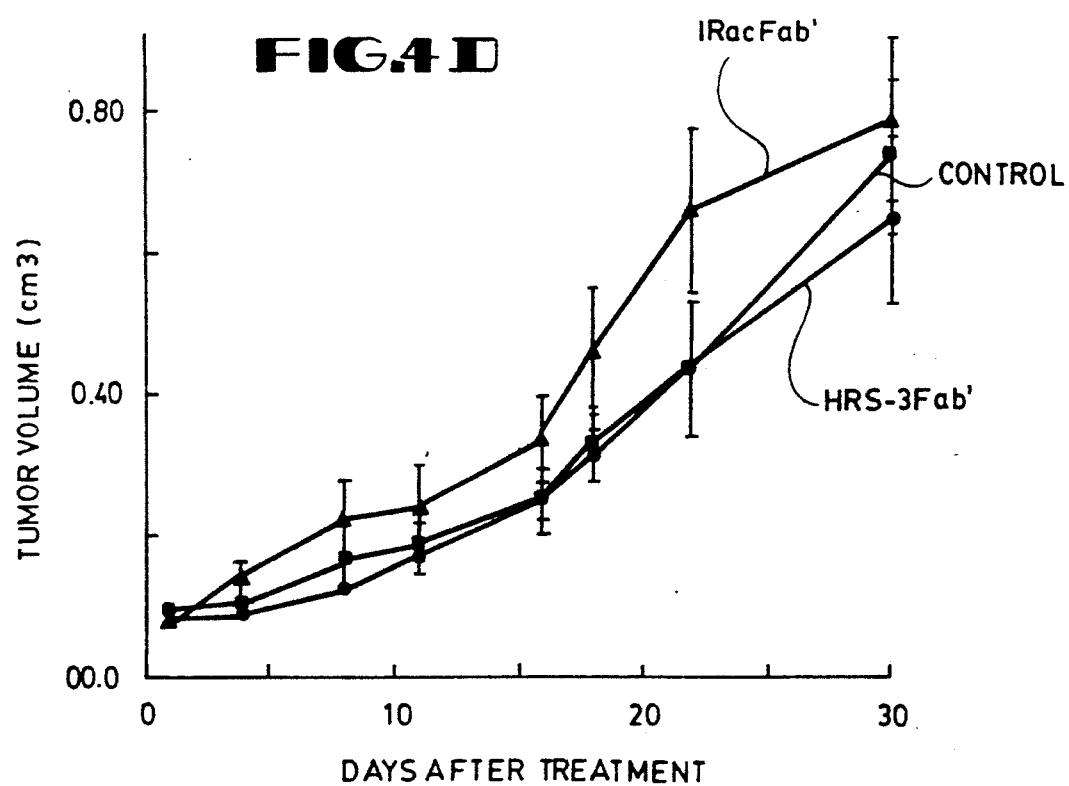

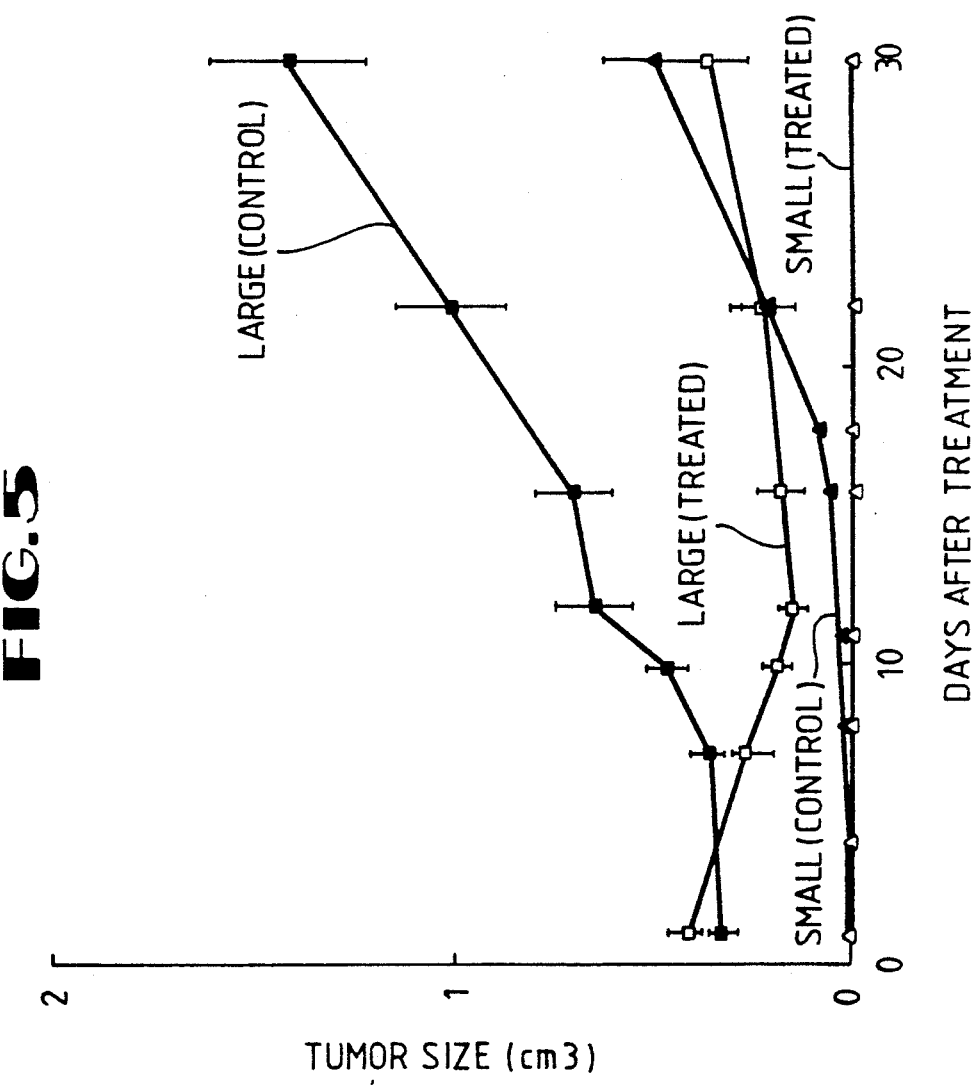

METHODS AND COMPOSITIONS FOR THE TREATMENT OF HODGKIN'S DISEASE

BACKGROUND OF THE INVENTION

1. Field of the Invention

This invention relates to methods and compositions useful in the treatment of patients suffering from Hodgkin's disease and other conditions such as large cell anaplastic lymphoma and graft-versus-host disease. In particular, this invention relates to antibody-toxin conjugates (immunotoxins) capable of selectively killing Hodgkin's and Reed-Sternberg cells and other cells such as activated lymphoid cells and monocytoid cells, and, in further embodiments, to hybridomas and antibodies useful in the preparation of such immunotoxins.

2. Description of the Related Art

Chemotherapy of Hodgkin's disease is undoubte of the major breakthroughs in clinical oncology over the last 25 years. The introduction of the multi-agent chemotherapy regimens such as MOPP (1) and ABVD (2) and the optimized use of radiation in early stages of the disease has improved the probability of curing these patients from less than 5% in 1963 to about 70% at the present time (3-5).

Despite the high proportion of cures in patients with Hodgkin's disease who respond to first line treatment, the outlook for those who relapse or fail to achieve complete remission is bleak. Second line combination chemotherapy can produce good remission rates although cures are uncommon (6-8). High dose chemotherapy with autologous bone marrow transplantation has been reported to be effective in relapsed or resistant cases of Hodgkin's disease (HD) but is associated with major toxicity, resulting in up to 26% treatment-related deaths (9,10). Of those patients achieving complete remission, 15-20% will develop a second malignancy as a chemotherapy-related side effect (11). There is therefore a need for new modes of treatment for this disease. In particular, there is a need for new agents for the management of or treatment of Hodgkin's disease that are free from mutagenic side effects.

An approach proposed by the present invention to preparing new, non-mutagenic reagents for the therapy of Hodgkin's disease would be to couple the ribosome-damaging A-chain of ricin or other toxins to antibodies directed against Hodgkin cell-associated antigens. In several laboratories, ricin A-chain has been linked to antibodies against tumour-associated antigens to form immunotoxin reagents that are selectively toxic to malignant cells in vitro (reviewed in 12,13). However, in vivo studies in rodents, and more recently, in man have given variable results. In rodents, good antitumor effects have generally been observed in leukemia and lymphoma models, whereas solid tumors appear to be less responsive (12,13). In humans, the antitumor effects obtained in melanoma (14) and leukemia (15) patients have so far been disappointing, whereas in patients with steroid-resistant graft-versus-host disease, remarkable benefit has been obtained (16).

Thus, although there have been many reports of the high cytotoxic potency and specificity of immunotoxins in vitro, relatively few workers have reported good antitumor effects of immunotoxins on solid tumors in vivo: Bernhard et al. (17) and Hwang et al. (18) reported that a single i.v. or s.c. injection of an abrin A-chain immuno-toxin reduced or completely abolished the growth of solid L10 hepatocarcinoma cell line tumors in guinea pigs. Leonhard et al. (19) described 11/46 complete remissions of solid human T cell line tumors in mice intravenously treated with CD5 ricin A-chain immunotoxins. Roth et al. (20) demonstrated a reduction in the number of pulmonary metastases after systemic administration of ricin A-chain immunotoxins to mice bearing TRF (transformed rat fibro-blasts) tumors. Others have needed to give multiple injections with dosages up to 125% of the $LD_{50}$ (21) or intratumoral injections to show antitumor effects of their immunotoxins (22). Accordingly, the use of immunotoxin in the treatment of tumour, particularly solid tumors, has heretofore been unpredictable at best.

For the foregoing and other reasons, it can be appreciated that there is currently a need for novel approaches to the treatment and control of patients suffering from Hodgkin's disease. In particular, there is a need for improved treatment modalities which exhibit one or more advantages over existing approaches to treatment. Furthermore, there is a need for treatments which may be employed in those cases where more traditional approaches have not proven effective. The present invention addresses one or more shortcomings in the art through application of immunotoxin technology.

SUMMARY OF THE INVENTION

The present invention addresses one or more deficiencies in the prior art by providing improved methods and compositions for the treatment of Hodgkin's disease, as well as other diseases such as those involving large cell anaplastic lymphoma or graft-versus-host disease. It is proposed that the methodology and compositions disclosed herein will provide a means for treating Hodgkin's disease and other diseases which are caused by activated lymphoid cells, monocytoid cells or CD30- or IRac-positive cells, through the application of immunotoxin technology, wherein a specific cell surface binding ligand is conjugated to a toxin moiety, with the binding ligand serving as a means for directing the toxin moiety to the cells to be treated, in this case, Hodgkin, Reed-Sternberg, activated lymphoid cells or monocytoid cells.

Thus, the invention provides, in a general sense, an immunotoxin conjugate which includes a cell-surface binding ligand comprised of an antibody or antibody fragment having binding affinity for Hodgkin or Reed-Sternberg cells, and a toxin moiety conjugated to the binding ligand by means of a disulfide linkage. As used herein, the term disulfide linkage is meant to refer to any means of connecting the toxin moiety to the binding ligand wherein the connecting means includes a disulfide bond. A disulfide or similar biologically releasable bond is important to the realization of a clinically active immunotoxin in that the toxin moiety must be capable of being released from the binding ligand once the binding ligand has entered the target cell. Numerous types of linking constructs are known, including simply direct disulfide bond formation between sulfhydryl groups contained on amino acids such as cysteine, or otherwise introduced into respective protein structures. However, the term "disulfide linkage" in also meant to include the use of a linker moiety which includes a disulfide bond, as discussed further herein below.

In certain preferred embodiments of the invention the conjugate will include a binding ligand which, prior to conjugation with a toxin moiety, will exhibit a binding affinity (i.e., Kd) of less than about 200 nM for the targeted antigen. The inventors have found that a binding affinity of much higher than 200 nM will generally not have a high enough binding affinity to be of particular usefulness in connection with the treatment of clinical disease. For the purposes of the present invention, the binding affinities will typically be measured with reference to a Hodgkin's disease-derived cell line such as the L540 cell line. Moreover, where a binding ligand is said to exhibit a Kd of less than about 200 nM for L540 Hodgkin's cells, this phrase is meant to imply the binding affinity of such a ligand for such cells when carried out in accordance with the procedures set forth hereinbelow in the examples.

Although it is believed that useful immunotoxins may be prepared where the binding ligand exhibits a Kd of less than about 200 nM for, for example, L540 Hodgkin cells, in more preferred embodiments the binding ligand will exhibit Kds that are significantly less than 200 nM. For example, binding affinity, in terms of Kd, of less than about 40 nM and even those less than about 20 nM will be particularly preferred for uses in accordance herewith. The present inventors have discovered that these high binding affinities may be achieved against certain particular antigens, including the 70 Kd antigen recognized by the IRac antibody or the CD-30 antigen, as discussed in more detail hereinbelow. Of course, it will nevertheless be necessary to screen hybridoma banks to identify monoclonal antibodies which exhibit the desired binding specificity and affinity. In any event, the inventors have been able to obtain binding ligands having extremely high binding affinities, for example, on the order of less than about 7 to about 27 nM for L540 Hodgkin cells for the most preferred binding ligands provided in accordance herewith.

An important aspect of the present invention is the ability to prepare immunotoxins which include not only a binding ligand with a high binding affinity, but more importantly, immunotoxins which themselves exhibit very high anti-cellular cytotoxicity. Cytotoxicity is not always directly related to binding affinity, and therefore the identification of monoclonal antibodies which can be employed in the preparation of highly cytotoxic immuno-toxins will not necessarily be evident from a high binding affinity. Therefore, in addition to identifying anti-bodies or binding ligands having high binding affinity, one will also desire to screen such antibodies for their ability to provide highly cytotoxic immunotoxins, as well as immunotoxins with little or no cross-reactivity with non-tumor cells. The present invention provides in certain embodiments immunotoxins having exceedingly high cytotoxicities, for example, as measured in terms of the concentration at which they will inhibit by 50% the proliferation, protein synthesis or some other vital function of the cells (i.e., the "$IC_{50}$"). Accordingly, in certain embodiments, the invention is directed to conjugates which exhibit an $IC_{50}$ of less than or equal to about $10^{-9}$M on the targeted Hodgkin's disease cells. However, as a useful reference, the inventors disclose the use of the L540 Hodgkin's cell line in an assay for measuring a relative $IC_{50}$ of the respective conjugate embodiments. The preparation of immunotoxin conjugates which exhibit an $IC_{50}$ of less than or equal to about $10^{-9}$M on L540 Hodgkin's disease cells is believed to be predictive of conjugates that will exhibit certain clinical advantages in accordance with the present invention. That is, those conjugates having an $IC_{50}$ of less than about $10^{-9}$M will be expected to exhibit a preferred degree of usefulness in treating Hodgkin's disease. However, in even more preferred embodiments, the invention is concerned with the preparation of conjugates which exhibit an $IC_{50}$ of less than or equal to about $10^{-10}$M on L540 Hodgkin's cells. It is believed that Hodgkin's directed immunotoxins having this very high degree of cytotoxicity will be of particular usefulness in the treatment of this disease.

In more particular embodiments, the inventors disclose herein the preparation of various immunotoxin conjugates which exhibit an $IC_{50}$ of between about $7 \times 10^{-10}$ and about $1 \times 10^{-11}$M when measured on L540 Hodgkin's cells. This range is exemplary of the range of $IC_{50}$ observed for the most preferred and clinically useful immunotoxin conjugates in accordance herewith.

While the present invention is not limited to the targeting of any one particular Hodgkin's disease cell antigen, it has been found that certain antigens are to be preferred over others, both in terms of the ability to generate high affinity antibodies and high specific activity immunotoxins for such antigens, but further in that these antigens are found to define highly selective immunotoxins. One such antigen is known as the CD-30 antigen complex. The CD-30 antigen (also known as the Ki-1 antigen) is composed of two non reducible subunits of 105 and 120 kDa molecular weight.

While it was at one time thought that the Ki-1 or CD-30 antigen was specific for Hodgkin or Reed-Sternberg cells, it has now been found on a variety of other cells, including large cell anaplastic lymphomas, peripheral T-cell lymphomas, cutaneous lymphoid infiltrates and tumor cells of embryonal carcinoma. Furthermore, the CD-30 antigen can be induced on B and T cells by phytohemagglu-tinin (PHA), human T-cell leukemia viruses 1 and 2 (HTLV 1 and 2) as well as Epstein-Barr virus. In any event, however, it has been found that the CD-30 antigen can be employed for the generation of highly useful immunotoxins in accordance herewith.

A second antigen which the inventors have found to be particularly useful for the targeting of Hodgkin's disease-directed immunotoxins is the 70 kDa antigen which has been characterized by Hsu et al. (47, 48) through the use of the IRac antibody. The IRac antibody was developed through the use of Hodgkin's disease cells from tumor samples which were purified and stimulated with phorbol acetate (TPA). In any event, the inventors have found that the IRac antibody is particularly useful both in the preparation of immunotoxins and in the identification of cross-blocking immunotoxins which might be similarly useful.

Of course, it is not intended that this invention be limited to antibodies against these particular anti-Hodgkin's disease cell antigens. It is proposed that a number of target antigens are known which can suitably be employed in the practice of the present invention. Other possible targets include, for example, the interleukin 2 (IL2) receptor alpha or beta chain (CD25 antigen), the CD15 antigen, HLA-DR, the transferrin receptor, the leukocyte common antigen (CD45), and the like (see, e.g., references 73-74). Through the application or use of the techniques or materials set forth or referred to herein, it is proposed that one will be able to prepare binding ligands having a suitable degree of binding affinity and capable of providing immunotoxins having a suitable degree of specific cytotoxicity.

Furthermore, culture deposits have been made of hybridomas which secrete particular preferred antibodies directed against either the CD-30 antigen (i.e., the HRS-3 antibody, has been deposited with the PHLS Centre for Applied Microbiology & Research, European Collection of Animal Cell Cultures, Division of Biologics, Porton Down, Salisbury, Wiltshire, England, on Nov. 16, 1989, as accession No. 89111607) as well as hybridomas which secrete the IRac antibody also deposited with the PHLS Centre on Nov. 16, 1989, as accession No. 8911608. As discussed in more detail hereinbelow, these monoclonal antibodies may be employed either directly or in the initial screening and identification of antibodies having specificity for these two respective antigens.

Thus, in certain embodiments, the present disclosure is further directed to the preparation of hybridomas which may be employed in the preparation of antibodies useful in the practice of the invention, including in particular, CD-30 or IRac antibodies which exhibit binding characteristics similar to HRS-3 or IRac. Techniques are disclosed herein which may be employed both in the preparation of hybridoma libraries which secrete anti-Hodgkin's disease cell antibodies, and in screening these libraries to identify and select hybridomas secreting antibodies having many, if not most, of the desirable attributes of HRS-3 or IRac.

In general, the hybridoma libraries are prepared through the application of known monoclonal antibody techniques, with some important modifications. Typically one will desire to employ as the initial immunogen in hybridoma development, a Hodgkin's disease or Reed-Sternberg cell, cell line or cell derived protein or fraction. Advantageously, one may simply desire to employ whole tumor cells for this purpose, preferably tumor cells from a Hodgkin's disease cell line such as the L428 or L540. Since one of the preferred antibody species, HRS-3, was prepared using the L540 cell line, one may typically desire to use this cell line as the starting immunogen. However, it should be pointed out that the other preferred species, IRac, was prepared using tissue from diseased patients. Thus, the use of tissue biopsy samples, for example, should not be excluded. In any event, following immunization and fusion of lymphoid cells with an appropriate fusion partner (e.g., X63Aj8.635 or P3-NS1/1-Ag4-1), one will desire to screen the resultant hybridomas in various manners to identify an appropriate colony.

One such screening will typically be to exclude hybridomas which secrete antibodies not directed against cell surface antigens of the Hodgkin's disease cells. These techniques are well known in the art. One might also wish to screen putative positives against other Hodgkin disease cell lines or tissues to ensure that the secreted monoclonal is more or less pan-reactive with Hodgkin's disease cells. Another screening might be performed to exclude antibodies that are reactive with normal tissues such as tonsils or other normal tissues, particularly "life-sustaining tissues" as discussed hereinbelow.

Further, to assist in identifying CD-30 monoclonal antibodies (or IRac related antibodies) having the particular desirable attributes of HRS-3 (or IRac), one may find advantages in the use of the cross-blocking assay disclosed herein, e.g., using the HRS-3 (or IRac) antibody itself as the competing antibody. Using the foregoing techniques, one will be enabled to identify anti-Hodgkin cell antibodies that will "compete" with the HRS-3 or IRac antibody for its particular CD-30 or 70 Kd antigen epitope, respectively. Antibodies identified in this manner should therefore be reactive with the same, or associated, CD-30 epitope as HRS-3, or 70 Kd antigen epitope as IRac, as the case may be.

However, in addition to the identification of antibodies reactive with the same or similar CD-30 epitope, it will further be preferred to select monoclonal antibodies having the additional desirable characteristics of HRS-3 or IRac, including their high binding affinity (i.e., low Kd), their ability to form highly cytotoxic immunotoxins against Hodgkin's disease cells, the exhibition of little or no binding to life-sustaining "normal" tissues, and even the ability of the stability of the underlying hybridoma and its ability to secrete useful quantities of the antibody.

In addition to their usefulness in the preparation of immunotoxins, it is proposed that the anti-Hodgkin's disease cell antibodies disclosed or otherwise enabled herein will find utility in other respects. For example, it is contemplated that these antibodies may be useful in therapeutic modalities directly without toxin conjugation, in that these antibodies apparently exhibit direct anti-cellular activities. Furthermore, it is contemplated that due to the highly selective nature of their binding to Hodgkin's disease antigens, it is proposed that these antibodies will find utility in diagnostic embodiments, such as in the performance of RIAs or ELISAs for disease diagnosis or for following the course of the disease. In any event, it is specifically pointed out that this aspect of the invention is not limited to the preparation of immunotoxins.

In certain embodiments, the invention is directed to binding ligands, such as antibodies on antibody fragments capable of at least about 70% cross-blocking of the HRS-3 or IRac binding to L540 Hodgkin's cells, when said binding ligand is present at about 100-fold excess with respect to said HRS-3 or IRac antibody. It is proposed that where a desired antibody is capable of cross-blocking the binding of HRS-3 or IRac to the extent of about 70% when the cross-blocking is carried out as disclosed hereinbelow, one will thereby identify a binding ligand having a particular utility in the preparation of immunotoxins in accordance herewith. Even more preferably, through the use of cross-blocking techniques one will be enabled to select binding ligands that will cross-block either the HRS-3 or IRac antibodies to the extent of at least about 90% cross-blocking.

In still further embodiments, it will be desirable to identify binding ligands that are essentially, effectively or pharmacologically free of binding affinity for normal tissues. As used herein, the term "essentially free of binding affinity for normal tissues" is intended to refer to binding ligands which exhibit little or no binding affinity for life-sustaining tissues, such as one or more tissues selected from bone marrow, colon, kidney, brain, breast, prostate, thyroid, gall bladder, liver, lung, adrenals, heart, muscle, nerve fibers, pancreas, skin, or other life-sustaining organ or tissue in the human body. The "life-sustaining" tissues that are the most important for the purposes of the present invention, from the standpoint of low cross-reactivity, include heart, kidney, central and peripheral nervous system tissues, liver and lung. By the term "little or no" binding is meant an antibody or antibody fragment, which, when applied to the particular tissue under conditions suitable for immuno-histochemistry, will elicit either no staining or a mixed staining pattern with only a few positive cells of large lymphoid or monocytoid morphology scattered among a field of mostly negative cells.

The origin or derivation of the antibody or antibody fragment (e.g., Fab', Fab or F(ab')$_2$) is not believed to be particularly crucial to the practice of the invention, so long as the antibody or fragment that is actually employed for immunotoxin preparation otherwise exhibits the desired properties. Thus, where monoclonal antibodies are employed, they may be of human, murine, monkey, rat, hamster, chicken or even rabbit origin. The invention therefore contemplates the use of human antibodies, "humanized" or chimaeric antibodies from mouse, rat, or other species, bearing human constant and/or variable region domains, single domain antibodies (e.g., DAbs), Fv domains, as well as recombinant antibodies and fragments thereof. Of course, due to the ease of preparation and ready availability of reagents, murine monoclonal anti-bodies will typically be preferred.

The ligand-toxin conjugate composition of the invention will typically comprise a Hodgkin cell binding ligand conjugated to a toxin moiety through a disulfide linkage. This is because it has been found that the disulfide linkage is important where one desires to employ a toxin moiety such as ricin A chain in connection with anti-cellular therapy. While the mechanism is not entirely clear, it appears as though a disulfide linkage allows decoupling of a toxin moiety such as a ricin A chain moiety delivered to target cells by the binding ligand, thereby freeing the A chain moiety to exert its anti-cellular effect in the cytosol.

It is proposed that the configuration of cross-linking between, e.g., ricin A chain and the binding function is an important consideration in that this configuration appears to play an important role pharma-ceutically. This is likely a function of a somewhat complex set of variables, including the vulnerability of the disulfide bond to "decoupling" as well as its ability to release the toxin upon binding on the surface of target cells.

The general construction of conjugates by means that will provide a disulfide bond between the ligand and the toxin moiety is generally known in the art, as reviewed in references such as 53 and 54. Disulfide coupling may be achieved directly between cysteine residues of the respective proteins, e.g., by means of disulfide exchange reactions wherein the protein is reduced and derivatized with Ellman's reagent. However, direct disulfide bond formation between many binding ligands and toxin will generally not be preferred, since a cysteine in the ligand is not accessible for coupling. Reduction of cysteine bridges in the ligand, to provide reactive SH groups, may damage the functional integrity of the ligand.

Accordingly, one will generally find it preferable, in the case of ligands lacking free cysteine residues, to employ a cross-linking group which will provide suitable release characteristics and resultant therapeutic parameters. A variety of cross-linkers having disulfide groups are known in the art, as exemplified by SPDP, SATA, 2-IT and SMPT (34, 54). Generally speaking, suitable cross-linkers will include structures 1) having the ability to covalently couple to amino groups of lysine, or the like; and 2) incorporating a disulfide or other desired releasable functionality. Useful groups of cross-linkers include the heterobifunctional cross-linkers described above.

Particular useful cross-linkers found to have desirable characteristics in terms of stability, yields and long in vivo half-lives of resulting conjugates include SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene). SPDB and SMPT generate linkages containing a hindered disulfide bond and are particularly preferred. A variety of additional reagents for the purposes of cross-linking conjugates in accordance with the present invention are known in the art and can be substituted for those referred to herein.

As used herein, the phrase "hindered disulfide bond" is intended to refer to a disulfide bond having groups near or adjacent to the disulfide bond that reduce its susceptibility to reduction, e.g., by thiols, by 3-fold or more, preferably greater than 5-fold, relative to the disulfide bonds generated by SPDP or 2-iminothiolane hydrochloride reagents. The rate of reduction of immunotoxin into the ligand and the toxin component may be measured, e.g., by treating a known concentration of immunotoxin with a known concentration of a thiol such as dithiothreitol or 2-mercaptoethanol and measuring the extent of dissociation of the immunotoxin at various time intervals. This measurement may be performed in a number of ways, e.g., by SDS-polyacrylamide electrophoresis and densitometric scanning of gels. By this approach, the ratio of the sum of the areas under the free antibody and free toxin peaks to the total area under all the peaks gives the fraction of immunotoxin that has dissociated.

The toxin molecule of the present invention will typically comprise a toxin A chain or toxic derivative thereof. Numerous A chains believed to have suitable anti-cellular properties in the practice of the invention are known in the art. Exemplary "A chains" which may be employed in connection with the invention, as this term is used herein, include the A chain of ricin, diphtheria toxin, volkensin, modeccin, Shigella toxin, abrin or the like; or the "free A chains", known as ribosome-inactivat-ing proteins, e.g., gelonin, trichosanthin, saporin, bryodin, momordin, alpha-sarcin, dianthins, pokeweed antiviral protein, barley toxin, or the like; or other known toxin moieties such as Pseudomonas exotoxin A, diptheria toxin, genetically engineered versions or derivatives of any of the foregoing toxins (see, e.g., ref. 73,74), intact ricin that has been "blocked" to prevent nonspecific B-chain binding (see, e.g., refs. 75-76), or fragments of any of the foregoing. Of these, the ricin A chain molecule is the most preferred due to its high intrinsic anti-cellular activity and the clinical experience in humans indicating only modest side effects.

In addition to the whole A chain molecule, one may desire to simply employ that portion of the A chain that is necessary for exerting anti-cellular effects. For example, it has been found that the ricin A chain molecule can be truncated by removal of the first 30 amino acids and nevertheless obtain a toxin molecule that exerts sufficient anti-cellular activity to be of use in connection herewith. Such termination is achieved by either genetic engineering or proteolytic degradation, e.g., with Nagarase (55), the product being referred to herein as "truncated" A chain.

In the more preferred embodiments of the present invention, .a deglycosylated A chain such as deglycosylated ricin A chain (dgA) or variants thereof is employed. Deglycosylated A chain is A chain that has been treated so as to remove or destroy carbohydrate moieties (e.g., mannose, fucose) which are incorporated into naturally produced A chain molecules. It has been found that the presence of mannose/fucose on the oligosaccharide side chains of the A chain promote rapid clearance by the liver and reduced therapeutic effect of the toxin or A chain by cells such as the reticuloendothelial cells of the liver and spleen which have receptors that recognize these structures. The inventors have found that, through the use of deglycosylated A chains, one may achieve particular advantages in terms of both increased potency and increased half life of the conjugate in the circulation and reduced hepatotoxicity, by reducing the clearance of the conjugate by the liver.

While deglycosylated ricin A chain is preferred, there is no reason that other nonglycosylated toxin A chains or ribosome-inactivating proteins could not be employed in connection with the invention. In any event, the preparation and use of deglycosylated A chain is known in the art as illustrated by references such as Thorpe et al. (30, 56). Moreover, deglycosylated A chain is now available commercially from Inland Laboratories, Austin, Tex.

Additionally, the preparation of ricin A chain by recombinant means is now known, as exemplified by O'Hare et al. (57). Thus, it is now possible to alter the amino acid structure through the application of in vitro muta-genesis technology. Through the judicious selection of amino acid sequence alterations or modifications based on knowledge of interactive forces between amino acids, one can readily modify or alter the A chain sequence and provide a means for selecting variant proteins having improved toxicity, pharmacologic or release properties.

In still further embodiments of the invention, it is contemplated that several binding ligands may be conjugated to a single toxin A chain moiety. It is proposed that such constructs, containing up to, for example, 5 or so binding ligands per toxin moiety, may find particular therapeutic benefits. It is, for example, believed that such constructs may have a particular high binding affinity for target cells, thereby providing enhanced ability to deliver toxin to the targeted cells and thereby kill them.

It has been found that ricin B-chains alone, or coupled to antibody, can serve to greatly enhance the specific cytotoxicity of immunotoxins containing ricin. B chains are the "lectin" binding regions of the toxin complex that are responsible for the native toxin's broad ranging cell-binding capability. It has been proposed by others that not only do B chains stimulate immunotoxin action, but that one can "separate" pharmacologically this action from the cell-binding function by chemical or heat modification of the B chain (58). It is thus proposed that the application of toxin B chains in combination with the A chain conjugates may provide advantages in terms of even further specific cytotoxicity against targeted cells.

An important aspect of the invention is the preparation of pharmaceutical compositions which incorporate the binding ligand-toxin conjugates in therapeutically effective amounts. Of course, where pharmaceutical compositions are prepared, one will desire to employ conjugates that are essentially free of unconjugated material and, further, do not contain any undesired impurities. Therefore, one will generally find it necessary to purify conjugates prepared in accordance with the invention through the application of purification technology. Techniques are known for isolating and purifying conjugates to a very high degree.

In certain aspects, the present invention is thus concerned with techniques for purifying immunoconjugates, including conjugates such as the anti-Hodgkin's cell ligand-toxin conjugates of the present invention. Parti-cular techniques which have been found useful in the purification of conjugates in accordance herewith include affinity chromatography techniques employing Blue- (or Red) Sepharose, molecular exclusion chromatography on Sephacryl or even gel permeation chromatography by HPLC. (See, e.g., U.S. Ser. No. 07/150,190, filed 1/29/88, incorporated herein by reference)

Pharmaceutical compositions comprising conjugates of the present invention are typically prepared by combining the purified conjugate with a pharmaceutically acceptable diluent or excipient for parenteral administration. A variety of suitable carrier vehicles and their formulation are described, for example, in reference 29. Suitable carriers include sterile aqueous solutions including stabilizing agents, e.g., buffers and other protein and pH-stabilizing agents, salts and the like. Typically, sterile aqueous compositions of the desired conjugate will include a dose concentration of between about 0.25 and about 2.5 mg/ml, to allow for administration of convenient amounts.

In certain embodiments, the appropriate dose of conjugate to be administered will be somewhat dependent upon the particular patient. Those of skill in the art of immunotoxin administration will appreciate that variations in optimal doses will exist from patient to patient, depending on a variety of variables. Typically, one will desire to administer on the order of 10 to 250 mg (for an average 70 kg human), depending upon the type of conjugate employed and the appearance of untoward side effects such as vascular leak syndrome (VLS), myalgia, fatigue and/or fever. Other considerations include the administration of the conjugates in 2-20 fractional doses.

In still further embodiments, the present invention is directed to the preparation of "cocktails" which incorporate more than one immunotoxin species. Prefer-ably, such cocktails employ immunotoxins having speci-ficity for different antigens on the Hodgkin's disease or Reed-Sternberg cells. For example, in particular preferred embodiments, one will desire to prepare a "cocktail" pharmaceutical composition which comprises one immunotoxin directed to the CD-30 antigen, and a second immunotoxin directed to the 70 kDa/IRac antigen. In these embodiments, one will typically desire to employ the respective immunotoxins in an overall amount such that their total toxicity will not be high enough to cause undesirable side effects. It is proposed that by the use of immunotoxins having differing specifities, one will decrease the opportunity for the development of resistant tumors, such as tumors wherein a single targeted antigen such as the CD-30 antigen is no longer being expressed. Where two or more independent epitopes on one or more antigens are targeted, such as through the use of such cocktails, it is believed that a much improved overall antitumor therapeutic effect will be realized.

BRIEF DESCRIPTION OF THE DRAWINGS

FIG. 2. Cytotoxicity of CD30 immunotoxins to L540 cells in vitro. In FIG. A, the cells were incubated for 48 hours, HRS-4.dgA (■), HRS-3.dgA (●), HRS-4.dgA (○), Ber-H2.dgA (▲), Ki-1.dgA (□). In FIG. 2B, the cells were incubated with HRS-3 Fab'.dgA (♦) and HRS-4 Fab'.dgA (○). Points geometric means of triplicate measurements of incorporated by the cells during the final 24 hour period of culture expressed as a percentage of the incorporation in untreated cultures. Bars, one SD about the mean unless smaller than the points as plotted.

FIG. 4. Antitumor effects of intact and Fab' immunotoxins on solid L540 tumors in triple beige nude mice. Tumors were approximately 0.5 cm diameter on the day of treatment (day 1). Groups of 8-10 animals, were injected i.v. in 200 ul as follows: FIG. 4A: (■) PBS, (●) HRS-3.dgA, (□) Ber-H2.dgA, (▲) IRac.dgA. FIG. 4B (■) PBS, (●) HRS-3 (□) Ber-H2, (▲) IRac. FIG. 4C: (■) PBS, (●) HRS-3 Fab'.dgA, (▲) IRac Fab'dg.A. FIG. 4D: (■) PBS, (●), HRS-3 Fab' (▲) IRac Fab'. The doses in terms of protein were 48 ug for intact immunotoxins, 40 ug for antibodies, 205 ug for Fab' immunotoxins and 129 for Fab' fragments. Bars represent the standard error of the mean.

FIG. 5 Treatment of large and small tumors with IRac.dgA. Large tumors were approximately 1 cm in diameter, small tumors were 2 mm. Groups of 8 animals were injected 200 ul of either PBS or 48 ug (protein) IRac.dgA on day 1 as follows: (■) PBS (large tumors) (□) IRac.dgA, (▲) PBS (small tumors), (△) IRac.dgA. Bars represent the standard error of the mean.

DETAILED DESCRIPTION OF THE PREFERRED EMBODIMENTS

Introduction

Figure 1:
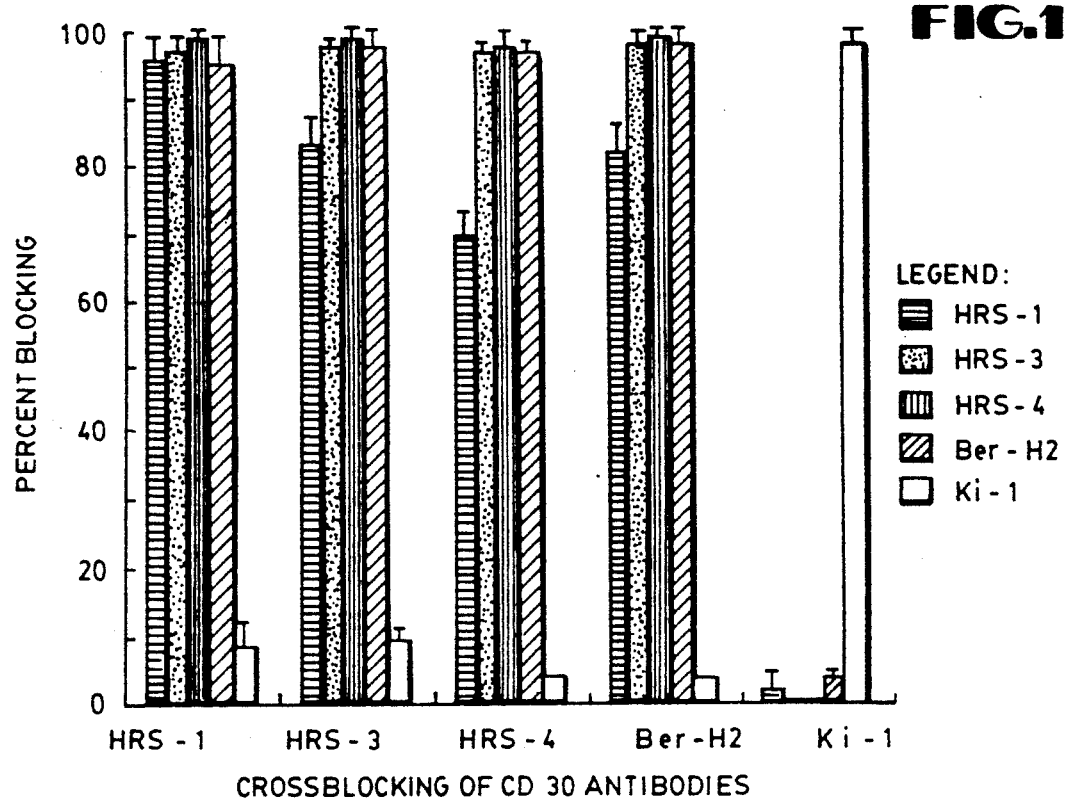
FIG. 1. Crossblocking of CD30MoAbs. $^{125}$I-labeled antibodies (0.5 ug) were mixed with a 100 fold excess (50 ug) of HRS-1, HRS-3, Ber-H2 and Ki-1 and were added to L540 cells in PBS/BSA/N$_3^-$ ° C. at 4° C. Each group of histograms shows the percent blocking (calculated as described in Example I) of one of the $^{125}$I-labeled antibodies (marked with an asterisk) by the different unlabeled antibodies. The vertical lines on the histograms show the standard deviation of triplicate determinations.

The present invention relates to the preparation and use of immunotoxins which recognize antigens located on the cell surface of Hodgkin and Reed-Sternberg cells. Immunotoxin conjugates of the invention are composed of a cell surface binding ligand, typically an antibody or antibody fragment such as an Fab' fragment, having binding affinity for cell surface antigens located on Hodgkin or Reed-Sternberg cells, with the binding ligand being conjugated to a toxin moiety by means of a disulfide linkage between the toxin and the binding ligand. The disulfide linkage may be formed by direct conjugation of the binding ligand to the toxin moiety, or may involve the use of a chemical linker which incorporates a disulfide group. The use and nature of the disulfide linker is thought to be important to the pharmacologic properties of the immunotoxin in that, preferably, the conjugate should remain intact while circulating through the blood stream, but, once the conjugate attaches itself to a target cell, the toxin moiety should be able to dissociate from the ligand and enter the cell to work its toxic effect upon the target.

The cell surface binding ligand employed in connection with the practice of the invention will typically be an antibody or antibody fragment having a degree of specificity or affinity for Hodgkin or Reed-Sternberg cells. Hodgkin's disease is one of the major cancerous diseases of the lymphoid system. It is characterized by an infiltration of the lymphoid organs by Hodgkin and Reed-Sternberg cells which results in a progressive enlargement of lymph nodes, spleen, liver and eventually an infiltration of bone marrow, lung and other organs, depending on the stage of the disease. Hodgkin's disease is considered to be a malignant neoplasm of transformed early lymphoid progenitor cells or of dendritic cells. The characteristic tumor cells in this disease are the mononucleated Hodgkin cells and the binucleated Reed-Sternberg cell, which are found in infiltrated tissue in association with lymphocytes and eosinophilic leukocytes and fibrosis. It has been proposed that the Reed-Sternberg cell may in fact be the clonal cell responsible for the malignant aspect of Hodgkin's disease, thus making such cells a principal target in any therapeutic regimen.

The exact nature of Hodgkin's disease has been disputed over the years. The suggested origin of Reed-Sternberg cells in Hodgkin's disease includes histiocytes, macrophages and B or T lymphocytes. It has been proposed that Hodgkin or Reed-Sternberg cells are probably related to histiocytes or interdigitating reticulum cells, in that it has been possible to identify phenotypic markers that are shared by Hodgkin or Reed-Sternberg cells, interdigitating reticulum cells and histiocytes.

The present invention takes advantage of the existence of antigenic cell-surface molecules that are found on Hodgkin or Reed-Sternberg cells, but are not found, or found in only limited amounts or degrees, on non-cancerous tissues. However, due to the presence of many such Hodgkin or Reed-Sternberg cell surface antigen on certain cell types such as interdigitating reticulum cells or activated T or B cells, immunotoxins of the present invention which employ antibodies which recognize these antigens may also be useful in treating conditions of these cells as well, such as graft-versus-host disease, organ or tissue allograft rejection episodes, autoimmune disorders, histiocytomatosis, histiocytosis X, large cell anaplastic lymphomas, or even lymphomatoid papulosis.

In any event, it will typically be the case that anti-Hodgkin or Reed-Sternberg antibodies which recognize antigens found on activated T or B cells, or on interdigitating reticulum cells, will nevertheless prove useful therapeutically and such a reactivity will not in itself present a problem of untoward reaction due to reactivity with these cells. Of course, it will not be desirable to employ antibodies which react with cells other than activated lymphoid cells or monocytoid cells in major normal or "life-sustaining" tissues. Reactivity with normal tissues such as these will tend to provide an immunotoxin that will not be of particular use clinically.

In a general sense, the preparation of antibodies having specificity for Hodgkin or Reed-Sternberg antigens can be accomplished using more or less standard hybridoma technology, but with some important modifications. For example, one will desire to employ Hodgkin or Reed-Sternberg cells or cell derived antigen(s) for the initial immunization of animals that are being employed to generate the hybridomas. In the preparation of antibodies, one may find particular advantage in the use of a Hodgkin disease cell line, such as the L-428, L540, DEV, L591, KM-H2 or even the HDLM cell line, which have been developed as permanent cell lines (see, e.g., references 66-68, 71 and 72) and can be employed as the initial immunogen.

For example, in the preparation of useful monoclonal antibodies in accordance herewith, one may desire to immunize a mammal such as a BALB/c mouse with whole L428 cells, or cells from another Hodgkin's disease cell line such as L540, obtain spleen cells from the immunized mouse and fuse the spleen cells with cells of, preferably, a non-secreting myeloma line that is compatible with the particular mammalian source that is being employed, such as X63-Ag8.653 (59) or Sp2/O-Ag14, in t he case where murine hybridomas are being employed. Although murine hybridomas are to be preferred due to their ease of preparation, as well as their general acceptability for use in connection with human administration, there is no reason why other mammalian sources of programmed spleen cells or lymphocytes cannot be employed where desired, including lymphocytes from humans, monkeys, rats, hamsters, chickens or even rabbits.

Additional advantages may be realized where, in addition to the use of Hodgkin cells for the initial immunization, one employs a means of stimulation of the Hodgkin cells in a manner which induces or enhances the appearance of Hodgkin related antigens. For example, one may employ substances such as phorbol esters (e.g., 12-O-tetra-decanoyl phorbol-13-acetate; TPA) which stimulate cellular differentiation, to enhance the appearance of desirable target epitopes on the cell surface of cells being employed for initial immunization in the preparation of anti-Hodgkin disease antibodies. Other agents which might be similarly useful include interleukin-1 (IL-1), phytohemagglutinin (PHA), Epstein-Barr virus, or even human T-cell leukemia virus 1 (HTLV-1).

Regardless of the type or origin of cells being employed for the initial generation of hybridoma banks, one will desire to screen the bank to identify those hybridomas which secrete antibodies having the desired binding capabilities. In general, for uses in accordance with the present invention, one will preferably desire to select those hybridomas which 1) secrete antibodies having a high affinity for the target cells, 2) are capable of forming immunotoxins which exhibit a low $IC_{50}$ (i.e., 50% inhibitory concentration), and 3) exhibit minimal binding to all or most normal tissues. These are the attributes that are believed to be most important in the formation of immunotoxins in accordance with the present invention.

The inventors have identified certain cell surface antigens that are associated with Hodgkin's disease or Reed-Sternberg cells which appear to provide particularly useful monoclonal antibodies in the foregoing regards. For example, antigens which have found particular utility in providing antibodies having particularly desirable attributes are the CD30 antigen complex and the 70 kd Hodgkin and/or Reed-Sternberg associated antigen. It should be appreciated, though, that the present invention contemplates that other Hodgkin or Reed-Sternberg associated antigens or epitopes can be employed in connection with the practice of the invention so long as antibodies against such or other antigens or epitopes exhibit the desired binding capacity, tissue selectivity and killing capability when formed into an immunotoxin.

The CD30 Antigen Complex

An important finding of the inventors is that CD30 immunotoxins directed against the Ki-1 antigen on Hodgkin cells may be identified which have high potency and specificity of cytotoxic effect and sufficiently restricted binding to normal human tissues that they are candidates for the treatment of Hodgkin's disease in man.

The Ki-1 antigen (CD30) was first described by Schwab et al., 1982 (23). It is composed of two nonreducible subunits of 105 and 120 kDa molecular weight (24). The antibody, which was raised against the Hodgkin cell line L428 (25), was originally thought to be specific for Hodgkin and Reed-Sternberg cells. It has since been demonstrated to be present on anaplastic large cell lymphomas (26), peripheral T cell lymphomas (26), cutaneous lymphoid infiltrates (27) and tumor cells of embryonal carcinoma (28). The Ki-1 antigen is not expressed on resting mature or precursor B or T cells, but it can be induced on these cells by PHA, HTLV1 and IL-1 or Epstein-Barr virus (EBV).

Since such induction is accompanied by the expression of other activation markers such as HLA-DR, transferrin receptor and Il-2 receptor it was concluded that Ki-1 identifies both activated normal T- and B-lymphocytes and lymphomas derived from such cells (26). Because the Ki-1 antigen is expressed on all cases of Hodgkin's disease apart from the lymphocyte-predominant subtype (27), and has very limited expression on normal tissue (26), it appears to be a good target for immunotherapy. One of the five CD30 antibodies tested in this study (HRS-4) exhibited a strong crossactivity with a vital organ (pancreas) that would reduce its clinical usefulness as an immunotoxin. Thus, it is now clear that certain CD30 immunotoxins are to be preferred over others.

The preparation of monoclonal antibodies against the CD30 complex can be achieved in a number of fashions. Typically and most readily, one employs a Hodgkin cell line such as the L428 or L540 line, and immunizes a selected mammal with the Hodgkin disease cells until an adequate immune response to the cells is obtained. Spleen cells from the immunized mammals are then employed in the preparation of hybridomas. Once a hybridoma bank has been obtained, one will desire to screen the bank to identify colonies which secrete antibodies having the desired pharmacokinetics, including binding strength (Kd), ability to form highly toxic immunotoxins $IC_{50}$), as well as tumor cell selectivity. For most purposes in accordance with the present invention, the inventors propose that useful monoclonal antibodies will be characterized by Kd of at least about 200 nM for L540 or L428 cells, and even more preferably less than about 40 or even 20 nM. The most preferred antibodies will have a binding affinity of between about 7 and about 27 nM for L540 cells, or even lower.

As discussed in more detail in the Examples hereinbelow, the inventors have identified certain monoclonal antibodies which have particularly desirable pharmacologic characteristics in terms of the criteria discussed above. The most preferred anti-CD30 antibodies identified exhibit very low Kds, very low $IC_{50}$s when incorporated into toxin A chain immunotoxins, and exhibit very low binding to non-tumor tissues. The most preferred of the anti-CD30 monoclonal antibody is known as HRS-3, and was originally developed by Dr. Michael Pfreundshuh. Hybridomas secreting HRS-3 have been deposited with the PHLS Centre for Applied Microbiology and Research and accorded accession No. 89111607.

While one may find particular benefit through the use of hybridomas which secrete HRS-3, other antibodies against the CD30 complex can be employed and nevertheless obtain useful results in accordance herewith. Moreover, one may desire to use the HRS-3 antibody itself as a means of identifying other useful antibodies. For example, a cross-blocking technique is set forth hereinbelow which will allow the identification and selection of antibodies which have the same or similar binding specificity as HRS-3. Thus, one may find some benefit in employing such a cross-blocking assay in the initial screening of hybri-doma clones to identify those which secrete antibodies capable of competing with the HRS-3 or other antibodies found to be useful in accordance herewith. Such other antibodies may then be further screened to identify those having additional useful and desirable attributes such as high binding capability and selectivity for Hodgkin cells, ability to form highly toxic immunotoxins, hybridoma stability, ability to secrete large amounts of antibody, stability of the antibody and resultant immunotoxin, ability to give Fab' fragments in good yield, and the like.

The 70 kDa Antigen

Another Hodgkin cell determinant has been identified which, in addition to the CD30 complex, has been found by the inventors to be particularly useful in the preparation of anti-Hodgkin or Reed-Sternberg cell immunotoxins. This antigen has been identified as a 60 or 70 kd Hodgkin cell surface antigen by Drs. P-L and S-M Hsu, who first charac-terized the antigen through the preparation of monoclonal antibodies having binding specificity for Hodgkin mono-nuclear cells and Reed-Sternberg cells (47, 48). One antibody developed by these individuals has been designated as "IRac" based on its ability to recognize the 70 kd antigen, which has been found to also be associated with inter-digitating reticulum ("IR") cells. In contrast to the HRS series antibodies which were developed through the use of Hodgkin disease cell lines, the IRac antibody was developed through the use of Hodgkin disease tissue samples from Hodgkin disease patients.

In particular, the IRac antibody was developed by immunizing mice with TPA-induced Hodgkin/Reed-Sternberg cells. The cells were obtained from surgical specimens from either lymph node or spleen of Hodgkin's disease patients which had been diagnosed based on established criteria. The sterile tumors were minced and filtered through a nylon mesh and the cells collected by Ficoll-Hypaque gradient centrifugation. The cells collected from the gradient were suspended in an appropriate medium (e.g., RPMI 1640 medium containing 10% fetal calf serum) and enriched by complement-mediated cytolysis of contaminating T cells, B cells and monocytes (60), followed by another round of centrifugation on Ficoll-Hypaque. Cells enriched in this manner were then cultured at about $4 \times 10^5$ to about $2 \times 10^6$ cells/ml in RPMI 1640 medium (Gibco) supplemented with 10% fetal calf serum, 2 mM glutamine, 50 uM 2-mercaptoethanol, and 50 ug/ml gentamycin at 37° C. in a humidified, 5% CO2 atmosphere. The developers of IRac have indicated that these cultures could be maintained for up to 7 days, with cell viability ranging from 70 to 80%.

For antigen induction, TPA was dissolved in DMSO at about 14 ug/ml and added to the above cell cultures at a final concentration of about 2 ng/ml, with fresh TPA containing medium being added about every second day. The induction was carried out for 3 days, and its effect monitored by immunocytochemical staining with anti-CD30 and anti-2H9 on cytospin smears. Successful induction was judged by the loss of CD30 and 2H9 from cell membranes, as well as cytologic changes, as evidenced by a decrease in the nuclear/cytoplasmic rations, increased size and number of cytoplasmic projections, as well as decreased cell proliferation. For generation of the IRac monoclonal, the procedure described for the generation of HeFi-1 and anti-2H9 was followed (61, 62). For intra-splenic immunization, a total of about $1 \times 10^7$ Hodgkin's disease-derived cells in 0.5 ml of RPMI medium was injected directly into the spleen of BALB/c mice, with a booster injection being given 21 days later, about 3-4 days prior to hybridization.

To screen for reactivities of monoclonal antibodies produced in the foregoing manner, the avidin-biotin-peroxidase (ABC)-immunoperoxidase technique was used on frozen sections of normal lymphoid tissue on cytospin smears of TPA-induced Hodgkin/Reed-Sternberg cells. Briefly, sections (or smears) were fixed in acetone at room temperature for 5 minutes. After being washed in Tris-buffered saline (TBS), 0.01M, pH 7.6, the sections or smears were incubated with hybridoma culture supernatant, and then with biotin-labeled horse anti-mouse Ig (1:200) and ABC. Each incubation lasted about 30-60 minutes, with an interval of about 5 minutes for washing with TBS. The slides were developed in a DAB-$H_2O_2$-$NiCl_2$ solution (63). Antibodies which had selective reactivity with the Hodgkin/Reed-Sternberg cells, but not with normal lymphoid cells, were subcloned and selected for further analysis.

Thus, the foregoing technique presents an alternative to the use of Hodgkin disease cell lines in the preparation of useful Hodgkin's disease cell directed monoclonal antibodies. The IRac antibody prepared through the application of the foregoing techniques has been deposited with PHLS Centre and accorded accession number 89111608. Thus, as with the anti-CD30 antibodies, and the HRS-3 antibody in particular, one might find particular benefit in the application of screening steps directed to the identification of antibodies which are capable of cross-blocking the binding of IRac for its epitope upon the 70 kd antigen species identified by Hsu et al.

Thus, for such studies, one might, e.g., wish to test hybridoma fluids for the ability of antibodies therein that effectively block the binding of IRac (or HRS-3, etc.) antibody for its epitope on target cells. A useful technique for measuring the cross-blocking ability is set forth hereinbelow in Examples I and II. Those hybridomas secreting antibodies capable of cross-blocking either HRS-3 or IRac to at least about 70%, or more preferably 80 or even greater than 90%, will be particularly preferred for uses in accordance herewith, assuming that such antibodies meet the additional preferred criteria of non-reactivity with most normal tissues, high binding affinities (i.e., low Kd) and high cytotoxicity when conjugated with toxin moieties.

Preparation of Immunotoxins

While the preparation of immunotoxins per se is, in general, well known in the art (see, e.g., U.S. Pat. Nos.

4,340,535, and EP 44167, both incorporated herein by reference), the inventors are aware that certain advantages may be achieved through the application of certain preferred technology, both in the preparation of the immunotoxins and in their purification for subsequent clinical administration. For example, while IgG based immunotoxins will typically exhibit better binding capability and slower blood clearance than their Fab' counterparts, Fab' fragment-based immunotoxins will generally exhibit better tissue penetrating capability as compared to IgG based immunotoxins.

Additionally, while numerous types of disulfide-bond containing linkers are known which can successfully be employed to conjugate the toxin moiety with the binding ligand, certain linkers will generally be preferred over other linkers, based on differing pharmacologic characteristics and capabilities. For example, the inventors have discovered that linkers which contain a disulfide bond that is sterically "hindered" are to be preferred, due to their greater stability in vivo, thus preventing release of the toxin moiety prior to binding at the site of action. Furthermore, while certain advantages in accordance with the invention will be realized through the use of any of a number of toxin moieties, the inventors have found that the use of ricin A chain, and even more preferably deglycosylated A chain, will provide particular benefits.

The most preferred toxin moiety for use in connection with the invention is toxin A chain which has been treated to modify or remove carbohydrate residues, so called deglycosylated A chain. The inventors have had the best success through the use of deglycosylated ricin A chain (dgA) which is now available commercially from Inland Laboratories, Austin, Tex.

However, it may be desirable from a pharmacologic standpoint to employ the smallest molecule possible that nevertheless provides an appropriate biological response. One may thus desire to employ smaller A chain peptides which will provide an adequate anti-cellular response. To this end, it has been discovered by others that ricin A chain may be "truncated" by the removal of 30 N-terminal amino acids by Nagarase (Sigma), and still retain an adequate toxin activity. It is proposed that where desired, this truncated A chain may be employed in conjugates in accordance with the invention.

Alternatively, one may find that the application of recombinant DNA technology to the toxin A chain moiety will provide additional significant benefits in accordance the invention. In that the cloning and expression of biologically active ricin A chain has now been enabled through the publications of others (64), it is now possible to identify and prepare smaller or otherwise variant peptides which nevertheless exhibit an appropriate toxin activity. Moreover, the fact that ricin A chain has now been cloned allows the application of site-directed mutagenesis, through which one can readily prepare and screen for A chain derived peptides and obtain additional useful moieties for use in connection with the present invention.

The cross-linking of the toxin A chain region of the conjugate with the binding ligand region is an important aspect of the invention. As discussed in the Summary section, where one desires a conjugate having biological activity, it is believed that a cross-linker which presents a disulfide function is required. The reason for this is unclear, but is likely due to a need for the toxin moiety to be readily releasable from the binding ligand once the ligand has "delivered" the toxin to the targeted cells. Each type of cross-linker, as well as how the cross-linking is performed, will tend to vary the pharmacodynamics of the resultant conjugate. Ultimately, one desires to have a conjugate that will remain intact under conditions found everywhere in the body except the intended site of action, at which point it is desirable that the conjugate have good "release" characteristics. Therefore, the particular cross-linking scheme, including in particular the particular cross-linking reagent used and the structures that are cross-linked, will be of some significance.

Cross-linking reagents are used to form molecular bridges that tie together functional groups of two different proteins (e.g., a toxin and a binding ligand). To link two different proteins in a step-wise manner, heterobifunctional cross-linkers can be used which eliminate the unwanted homopolymer formation. An exemplary heterobifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., dgA).

The spacer arm between these two reactive groups of any cross-linkers may have various length and chemical composition. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents).

The most preferred cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to its delivery to the site of action by the binding ligand. The SMPT cross-linking reagent, as with many other known cross-linking reagents, lends the ability to cross-link functional groups such as the SH of cysteine or primary amines (e.g., the epsilon amino group of lysine). Another possible type of cross-linker includes the heterobifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

Although the "hindered" cross-linkers will generally be preferred in the practice of the invention, non-hindered linkers can be employed and advantages in accordance herewith nevertheless realized. Other useful cross-linkers, not considered to contain or generate a protected disulfide, include SATA, SPDP and 2-iminothiolane (53). The use of such cross-linkers is well understood in the art.

Once conjugated, it will be important to purify the conjugate so as to remove contaminants such as unconjugated A chain or binding ligand. It is important to remove unconjugated A chain because of the possibility of increased toxicity. Moreover, it is important to remove unconjugated binding ligand to avoid the possibility of competition for the antigen between conjugated and unconjugated species. In any event, a number of purification techniques are disclosed in the Examples below which have been found to provide conjugates to a sufficient degree of purity to render them clinically useful. In general, the most preferred technique will incorporate the use of Blue-Sepharose with a gel filtration or gel permeation step. Blue-Sepharose is a column matrix composed of Cibacron Blue 3GA and agarose, which has been found to be useful in the purification of immunoconjugates (69). The use of Blue-Sepharose combines the properties of ion exchange with A chain binding to provide good separation of conjugated from unconjugated binding.

The Blue-Sepharose allows the elimination of the free (non conjugated) binding ligand (e.g., the antibody or fragment) from the conjugate preparation. To eliminate the free (unconjugated) toxin (e.g., dgA) a molecular exclusion chromatography step is preferred using either conventional gel filtration procedure or high performance liquid chromatography.

After a sufficiently purified conjugate has been prepared, one will desire to prepare it into a pharmaceutical composition that may be administered parenterally. This is done by using for the last purification step a medium with a suitable pharmaceutical composition.

Suitable pharmaceutical compositions in accordance with the invention will generally comprise from about 10 to about 100 mg of the desired conjugate admixed with an acceptable pharmaceutical diluent or excipient, such as a sterile aqueous solution, to give a final concentration of about 0.25 to about 2.5 mg/ml with respect to the conjugate. Such formulations will typically include buffers such as phosphate buffered saline (PBS), or additional additives such as pharmaceutical excipients, stabilizing agents such as BSA or HSA, or salts such as sodium chloride. For parenteral administration it is generally desirable to further render such compositions pharmaceutically acceptable by insuring their sterility, non-immunogenicity and non-pyrogenicity. Such techniques are generally well known in the art as exemplified by reference 70. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biologics standards.

A preferred parenteral formulation of the HRS-3.dgA or IRac.dgA is 0.25 to 0.5 mg conjugate/ml in 0.15M NaCl aqueous solution at pH 7.5 to 9.0. A preferred parenteral formulation of the HRS-3 Fab'.dgA is 1.0 to 2.5 mg/ml in 0.15M NaCl aqueous solution at pH 7.5. The preparations may be stored frozen at −10° C. to −70° C. for at least 1 year.

The following examples are representative of techniques employed by the inventors in the preparation and use of exemplary and preferred immunotoxins for use in the treatment of Hodgkin's disease and other conditions involving activated lymphocytes or neoplastic histiocytes or lymphoid cells. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLE I

Evaluation of Ricin A-chain Containing Immunotoxins Directed Against CD30

I. Materials and Methods

A. Materials

Tissue culture medium RPMI 1640 and fetal calf serum were purchased from Gibco-Biocult Ltd. (Paisley, Scotland). Blue Sepharose CL-6B, Sepharose G25 (fine grade), Staphylococcal protein A-Sepharose, DEAE Sepharose and Sephacryl S-200 HR were obtained from Pharmacia Ltd. (Milton Keynes, England). Carrier free [$^{125}$I] Iodine and L-[4,5-$^3$H] leucine (TRK 170) were purchased from Amersham International (Amersham, England). IODO-GEN was from Pierce Ltd. (Chester, England). Pepsin was from Sigma (Poole, England). Silicone fluids Dow Corning 200/1CS, 5CS and 550 were purchased from Dow Corning Corp. (Midland, USA).

B. Cells

The cell line L540, which derived from a patient with Hodgkin's disease (25) was maintained in RPMI 1640 supplemented with 20% (v/v) fetal calf serum, 4 mM L-glutamine, 200 U/ml penicillin and 100 ug/ml streptomycin.

C. Preparation of dgA

The ricin A-chain was purified by the method of Fulton et al. (29). Deglycosylated ricin A was prepared as described by Thorpe et al. (30). For conjugation with antibodies or Fab' fragments, the A-chain was reduced with 5 mM DTT and subsequently separated from DTT by gel filtration on a column of Sephadex G25 in PBS, pH 7.5.

D. Antibodies

Five monoclonal antibodies which recognize the Ki-1 antigen (CD30) were used in this study: HRS-1, HRS-3, HRS-4, Ber-H2 and Ki-1, of which the preparation of HRS-1, Ber-H2 and Ki-1 have been previously described (31,32,23). The characteristics of these antibodies are summarized in Table 1. HRS-1, Ber-H2 and Ki-1 were separated from the ascitic fluid of hybridoma bearing BALB/c mice by affinity chromatography on Staphylococcal protein A-Sepharose. HRS-3 and HRS-4 were purified from ascitic fluid by ammonium sulfate precipitation and ion exchange chromatography on DEAE-Sepharose.

MRC OX7, a mouse IgGl monoclonal antibody recognizing the Thy-1.1 antigen, was prepared from ascitic fluid as described by Mason and Williams (33) and was used as a nonspecific control antibody. The antibody preparations were >90% pure when analyzed by SDS-PAGE.

The preparation of the HRS-3 antibody proceeded in a manner similar in many respects to that of HRS-1 and HRS-2 described in reference 31, with a few modifications. BALB/c mice (4–6 weeks old) were immunized against HD cell line L540 cells according to the protocol referred to in reference 31, and the resultant lymphoid cells were fused with X63Aj8.635 cells. The fusion products were selected by standard techniques, and about 1114 positive growing clones were obtained. The supernatants of these clones were initially screened to identify those reactive with surface antigens (POK) and intracellular (APAAP) antigens, and from this screening 116 clones were selected for further screening. After histological screening to exclude those reactive with tonsils, only about 37 candidates remained. A second screening was then undertaken using other Hodgkin's disease cell lines as targets, after which 6 candidates remained. Of these 6 clones, two clones, designated HRS-3 and HRS-4, were characterized and employed in further studies.

TABLE I

| Characteristics of CD 30 Antibodies | | | |
|---|---|---|---|
| Antibody | Subclass | Immunogen | Reference |
| HRS-1 | IgG2a | L 428 | Pfreundschuh et al, 1988 |
| HRS-3 | IgG1 | L 540 | Pfreundschuh et al, 1988 (Unpublished) |
| HRS-4 | IgG1 | L 540 | Pfreundschuh et al, 1988 (Unpublished) |
| Ber-H2 | IgG1 | L 428 | Schwarting et al, 1987 |
| Ki-1 | IgG3 | L 428 | Schwab et al, 1982 |

E. Preparation of Fab' fragments

HRS-3 and HRS-4 were dialysed into 0.1 M citrate buffer, pH 8.0, and concentrated by ultrafiltration (Amicon, PM10 membrane) to 7.5 mg/ml. The pH was reduced to 3.7 by addition of 1M citric acid and the antibody solutions were subsequently incubated for four hours at 37° C. with pepsin (enzyme:protein ratio, 1/6 by weight). The digestion was terminated by raising the pH to 8.0 with 1M Tris buffer. The F(ab')$_2$ fragments were isolated by gel filtration on columns of Sephacryl S-200HR equilibrated in PBS, pH 7.5. F(ab')$_2$ fragments were reduced to Fab' monomers with 1-5 mM DTT. Residual DTT was removed by gel filtration on Sephadex G-25.

F. Preparation of Immunotoxins

IgG immunotoxins were prepared using the SMPT linker as described by Thorpe et al. (34). Briefly, SMPT dissolved in DMF was added to the antibody solution (7.5 mg/ml in borate buffer, pH 9.0) to give a final concentration of 0.11 mM. After 1 hr the derivatized protein was separated from unreacted material by gel chromatography on a Sephadex G25 column and mixed with freshly reduced ricin A-chain. The solution was concentrated to about 3 mg/ml and allowed to react for 3 days. Residual disulfide groups were inactivated by treating the immunotoxin with 0.2 mM cysteine for 6 hours. The solution was then filtered through a Sephacryl S200 HR column in 0.1M Phosphate buffer, pH 7.5 to remove unreacted ricin A, cysteine and aggregates. Finally, the immunotoxin was separated from free antibody by chromatography on a Blue Sepharose CL-6B column equilibrated in 0.1M sodium phosphate buffer, pH 7.5, according to the method of Knowles and Thorpe (24).

Fab' immunotoxins were prepared according to Ghetie et al. (35). Briefly, Fab' fragments (5 mg/ml in 0.1 M sodium phosphate buffer, pH 7.5 containing 1 mM EDTA) were derivatized with DTNB (Ellman's reagent) at a final concentration of 2 mM. Unreacted DTNB was removed by gel filtration on a Sephadex G25 column equilibrated in PBS. The derivatized Fab' fragments which contained 1-2 activated disulfide groups were allowed to react with a 1.5 fold molar excess of freshly reduced A-chain for 2 hours at room temperature. The Fab'.dgA immunotoxins were subsequently purified on Sephacryl S200 HR and Blue Sepharose columns as described for IgG immunotoxins.

The A-chain component of all the immunotoxins fully retained its ability to inhibit protein synthesis in rabbit reticulocyte lysates (36) after the A-chain had been released from the immunotoxins by reduction with DTT.

G. Radioiodination

Monoclonal antibodies were labeled with carrier free $^{125}$I using the IODO-GEN reagent to a specific activity of approximately 1 uCi/ug as described (37). Briefly, 500-750 ug of antibody in 100 ul borate buffer were incubated with 0.7 mCi of Na $^{125}$I in glass tubes coated with 8 ug of IODO-GEN for 10 minutes at room temperature. Free iodide was removed by gel chromatography on a Pharmacia PD 10 column. The radioiodinated antibodies fully retained their capacity to bind to L540 cells, as shown by their ability to compete equally with unlabeled antibodies for binding to cell antigens when applied at saturating concentrations (33).

H. Crossblocking Experiments

Triplicate samples of L540 cells ($5 \times 10^6$ cells/ml, 100 ul) in PBS containing 2 mg/ml BSA and 0.2% (w/v) NaN$_3$ (PBS/BSA/N$_3^-$) were mixed with $^{125}$I-labeled antibody (ug/ml, 100 ul) and a 100 fold excess of various unlabeled antibodies. The samples were then incubated for 30 minutes at 4° C. The cells were washed three times with PBS and the radioactivity of the pellet was measured using a Packard Multi-Prias 1 gamma counter. Blocking of labeled antibody was calculated as follows:

% blocking =

$$1 - \left( \frac{\text{cpm in presence of blocking antibody}}{\text{cpm in presence of nonspecific antibody}} \right) \times 100$$

I. Scatchard Analysis $^{125}$I-labeled antibody (50 ul) at various concentrations (0.25-32 ug/ml) was mixed for one hour at 4° C. with L540 cells ($2 \times 10^6$ cells/ml, 50 ul) in PBS/BSA/N$_3^-$. The cells were separated from the supernatant by centrifugation (12,000 x g, 1 min) through 75 ul of a mixture of 8.8% (v/v) Dow Corning silicone fluid 200/1CS, 7.2% 200/5CS and 84% Dow Corning 550. The Eppendorf tubes were then snap-frozen and the tips containing the cell pellets were cut off. The radioactivity in the cell pellet and in the supernatant were measured. The amount of radiolabeled nonspecific OX7 antibody that bound to the cells under identical conditions was substracted from the total amount of radiolabeled specific antibody that was associated with the cells to obtain the amount of specific antibody that was attached to cell antigens. The dissociation constant (K$_d$) and the number of molecules of antibody bound per cell under equilibrium conditions were calculated by analysing the data according to the method of Scatchard (38).

J. FACS Analyses

L540 cells ($10^6$ cells/ml, 100 ul) in PBS/BSA/N$_3^-$ were incubated in the cells of a rigid u-bottomed 96 well microtitre plate for 15 minutes at 4° C. with antibodies, Fab' fragments or immunotoxins (100 ul) at concentrations ranging from 0.001 to 100 ug/ml. The cells were washed three times with PBS/BSA/N$_3^-$ and were treated with FITC-labeled goat anti-mouse immunoglobulin (30 ug/ml, 100 ul) in PBS/BSA/N$_3^-$ for 15 minutes. The cells were then again washed three times with PBS/BSA/N$_3^-$ and analyzed on a FACS IV (Becton-Dickinson, Oxnard, USA). The molar concentrations of antibody and immunotoxin which gave 50% of the maximal fluorescence (i.e., under saturating conditions) were determined.

K. Cytotoxicity Assays

L540 cells suspended at $4 \times 10^5$ cells/ml in complete medium were distributed in 100 ul volume into the wells of 96-well flat-bottomed microtitre plates. Immunotoxins in the same medium were added (100 ul/well) and the plates were incubated for 24 h at 37° C. in an atmosphere of 5% $CO_2$ in humidified air. After 24 hours, the cells were pulsed with 1 uCi [$^3$H]-leucine for another 24 hours. The cells were then harvested onto glass fibre filters using a Titertek cell harvester and the radioactivity on the filters was measured using a liquid scintillation spectrometer (LKB, Rackbeta). The percent reduction in [$^3$H]-leucine incorporation, as compared with untreated control cultures, was used as the assessment of killing (35).

L. Immunoperoxidase Staining of Human Tissues

Cryostat sections of normal human tissues were treated with antibodies and stained using the ABC immunoperoxidase method, the three layer immunoperoxidase method or the APAAP technique that have been described in detail elsewhere (23,26,31,39).

II. Results

A. Crossblocking of CD30 MoAbs

These studies were conducted to determine whether the five antibodies recognize the same or different epitopes on the CD30 antigen. The results are shown in FIG. 1. HRS-1, HRS-3, HRS-4 and Ber-H2 crossblocked each others' binding to L540 cells but were not blocked by Ki-1. HRS-1 was slightly less effective at blocking HRS-3, HRS-4 and Ber-H2 binding than were HRS-3, HRS-4 and Ber-H2 at blocking each others' binding, probably because it has lower affinity. Ki-1 was only blocked by itself and did not block the other four antibodies.

Thus, there appear to exist at least two epitopes on the CD30 antigen, one of which is recognized by HRS-1, HRS-3, HRS-4 and Ber-H2 and the other by Ki-1.

B. Scatchard Analyses of the Binding of Intact Antibodies and Fab' Fragments

Table 2 summarizes the results of the Scatchard analyses of the binding of the five intact antibodies and the two Fab' fragments tested. HRS-4 had the highest avidity for L540 cells ($K_d = 7$ nM). Ber-H2 and HRS-3 had the next highest avidity with $K_d$ values of 14 nM and 15 nM respectively. The most weakly binding antibodies were HRS-1 and Ki-1 which had $K_d$ values of 160 nM and 380 nM respectively.

TABLE II

| | Scatchard Analyses of CD 30 Antibodies and Fab' Fragments | |
|---|---|---|
| Antibody | $K_d$ (nM ± sd)[1] | No. of molecules at saturation |
| HRS-1 | 160 ± 40 | 1.6 ± 0.3 × 10$^6$ |
| HRS-3 | 15 ± 3 | 1.7 ± 0.4 × 10$^6$ |
| HRS-3Fab' | 27 ± 10 | 3.2 ± 0.5 × 10$^6$ |
| HRS-4 | 7. ± 4 | 1.7 ± 0.2 × 10$^6$ |
| HRS-4Fab' | 17 ± 3 | 2.8 ± 0.4 × 10$^6$ |
| Ber-H2 | 14 ± 4 | 1.6 ± 0.3 × 10$^6$ |
| Ki-1 | 380 ± 90 | 1.7 ± 0.2 × 10$^6$ |

[1]Values of $K_d$ are the arithmetic mean and standard deviation of the results from 3 separate experiments The intact antibodies bound to L540 cells more avidly than their Fab' fragments. The difference was 1.8 fold for HRS-3 and 2.4 fold for HRS-4. This is due to the fact that intact antibodies can bind two antigens per cell, whereas the monovalent Fab' fragments bind to one antigen. In accordance with this, the number of Fab' molecules bound per L540 cell at saturation exceeds the number of intact antibodies by a factor of 1.6–2.0. The high absolute number of molecules bound (1.6–1.7 × 10$^6$ for intact antibodies) may be because L540 cells are large, having approximately eight times the volume of, for example, human B lymphocytes.

C. Cytofluorimetric Comparison of the Binding of Immunotoxins and Native Antibodies to L540 Cells The ability of the immunotoxins to bind to L540 cells was compared with that of the native antibodies and Fab' fragments using a cytofluorimetric assay. The concentrations of immunotoxin or antibody that gave half the maximal fluorescence are listed in Table III. These values allow the relative binding abilities of antibodies and immunotoxins to be compared (33) but are not themselves true measures of affinity/avidity because, unlike with the Scatchard analyses above, an indirect labeling technique is used. All the immunotoxins bound to L540 cells 1.6–3.8 fold more weakly than did their parental antibodies and Fab' fragments. The lower binding capacity of the immunotoxins can be explained either by steric hindrance by the A-chain moiety or by a loss of antibody affinity due to the chemical and physiochemical procedures used to prepare the immunotoxins.

TABLE III

| Binding Capacity of CD 30 Antibodies and Immunotoxins Compared by Cytofluorimetric Analysis | | |
|---|---|---|
| | Concentration giving 50% maximal fluorescence (nM + sd) | |
| | Unconjugated antibody | Immunotoxin |
| HRS-1 | 240 ± 140 | 900 ± 333 |
| HRS-3 | 3.0 ± 0.7 | 6 ± 1 |
| HRS-3Fab' | 23 ± 9 | 57 ± 27 |
| HRS-4 | 1 ± 0.5 | 3 ± 1 |
| HRS-4Fab' | 15 ± 6 | 33 ± 20 |
| Ber-H2 | 2.5 ± 1 | 4 ± 1 |
| Ki-1 | 310 ± 110 | 1000 ± 320 |

D. Cytotoxicity of Immunotoxins to L540 Cells

A representative cytotoxicity experiment is shown in FIG. 2 and the results of several experiments are summarized in Table IV. The IgG immunotoxins fall into two groups. The immunotoxins derived from the high affinity antibodies, HRS-3, HRS-4 and Ber-H2, were powerfully toxic and inhibited protein synthesis by L540 cells by 50% at concentrations (IC$_{50}$) of 0.9, 1.0 and $2.0 \times 10^{-10}$ M respectively; by contrast, the immunotoxins derived from the low affinity antibodies, HRS-1 and Ki-1, were weakly effective with IC$_{50}$ values of $0.8–1.0 \times 10^{-8}$ M respectively. The potency of the two most powerful immunotoxins, HRS-3.dgA and HRS-4.dgA, was only 15-fold less than that of ricin itself. The cytotoxic effect of all the immunotoxins was specific since the native antibodies and OX7.dgA, an immunotoxin that does not bind to L540 cells, were not toxic at $10^{-6}$M.

The immunotoxins prepared from the Fab' fragments of HRS-3 and HRS-4 were also highly toxic to L540 cells, with IC$_{50}$ values of 7.0 and $3.0 \times 10^{-10}$M respectively. These immunotoxins were therefore only 7.8 and 3.0-fold less toxic, respectively, than their intact IgG.-dgA counterparts. The lower activity of the Fab' immunotoxins is consistent with the findings of others (35,40,41) and is explained by the 1.8-2.4-fold lower affinity of the monovalent Fab' fragments compared with their divalent IgG counterparts.

TABLE IV

Cytotoxicity of CD 30 Immunotoxins on L 540 Cells

| Material | IC$_{50}$ (M) | No. of experiments |
| --- | --- | --- |
| HRS-1.dgA | $8.0 \pm 2.0 \times 10^{-9}$ | 3 |
| HRS-3.dgA | $9.0 \pm 0.8 \times 10^{-11}$ | 5 |
| HRS-3Fab'.dgA | $7.0 \pm 1.5 \times 10^{-10}$ | 3 |
| HRS-4.dgA | $1.0 \pm 0.4 \times 10^{-10}$ | 7 |
| HRS-4Fab'.dgA | $3.0 \pm 0.7 \times 10^{-10}$ | 3 |
| Ber-H2.dgA | $2.0 \pm 0.5 \times 10^{-10}$ | 3 |
| Ki-1.dgA | $1.0 \pm 0.5 \times 10^{-8}$ | 3 |
| Ricin | $6.0 \pm 2.0 \times 10^{-12}$ | 4 |
| Ricin A | $8.0 \pm 3.2 \times 10^{-7}$ | 2 |
| OX7.dgA | $>1 \times 10^{-6}$ | 2 |

E. Immunohistological Staining Pattern of Normal and Malignant Human Tissue

As shown in Table V, the pattern of reactivity of the five CD30 antibodies was very similar with the exception of HRS-4 which unexpectedly stained normal pancreatic tissue. They all strongly stained Hodgkin's disease tissue although there was a tendency in the lymphocyte dominant subtype to give weaker staining.

All the antibodies reacted with a few rare cells in the bone marrow, liver, lymph nodes, skin, spleen and thymus. These cells appeared to be large mononuclear cells in accordance with the finding that the antibodies stain activated lymphocytes (26). No staining was seen in the colon, kidney or lung.

TABLE V

Reactivity of CD 30 Antibodies with Normal and Malignant Cells of Various Tissues

| | HRS-1 | HRS-3 | HRS-4 | Ber-H2 | Ki-1 |
| --- | --- | --- | --- | --- | --- |
| Bone Marrow | −/+ [a] | −/+ [a] | −/+ [a] | −/+ [a] | −/+ [a] |
| Colon | − | − | − | − | − |
| Kidney | − | − | − | − | − |
| Liver | −/+ [b] | −/+ [b] | −/+ [b] | −/+ [b] | −/+ [b] |
| Lung | − | n.d. | n.d. | − | − |
| Lymph Nodes and Tonsil | + [c] | + [c] | + [c] | + [c] | |
| Pancreas | − | − | +++ | − | − |
| Skin | −/+ [d] | −/+ [d] | −/+ [d] | − | |
| Spleen | −/+ [e] | −/+ [e] | −/+ [e] | −/+ [e] | −/+ [e] |
| Thymus | −/+ [a] | −/+ [a] | −/+ [a] | −/+ [a] | −/+ [a] |
| Breast carcinoma | − | − | − | − | − |
| Colon carcinoma | − | − | − | n.d. | n.d. |
| Hodgkin's disease | +++ | +++ | +++ | +++ | +++ |
| Lung carcinoma | − | − | − | n.d. | n.d. |
| Ovary carcinoma | n.d. | − | − | n.d. | n.d. |
| Pancreas carcinoma | − | − | − | n.d. | n.d. |
| Stomach carcinoma | − | − | − | n.d. | n.d. |
| Thyroid carcinoma | n.d. | − | − | n.d. | n.d. |

−: no staining; +: weak staining; ++: moderate staining; +++: strong staining
−/+: mixed staining pattern as follows:
[a] very few positive cells
[b] few positive Kupffer cell like cells
[c] few positive large cells around, between and at the inner rim of the follicular mantles
[d] few positive Histiocyte like cells
[e] few positive large cells in the white pulp The strong staining of pancreatic tissue by HRS-4 alone may preclude the use of this antibody for therapy. Evidently, antibodies that recognize the same epitope on the immunizing antigen differ in primary sequence in a way that can lead to spurious cross-reactivity with normal tissues. Similar unpredictable cross-reactivity has been observed with CD22 antibodies by Li et al. (42).

III. DISCUSSION OF EXAMPLE I STUDIES

The cross-blocking studies performed on the five CD30 antibodies set forth in the present example indicate that there are at least two epitopes on the CD30 antigen. One epitope is recognized by HRS-1, HRS-3, HRS-4 and Ber-H2 and the other is recognized by Ki-1. This accords with the findings of Schwarting et al. (32) who demonstrated by FACS analyses that Ki-1 and Ber-H2 recognize different epitopes and of Pfreundschuh et al. (31), who found no cross-blocking between HRS-1 and biotinylated Ki-1.

HRS-3, HRS-4 and Ber-H2, which bound most strongly to L540 Hodgkin cells ($K_d$=15 nM, 7 nM, 14 nM), formed the most potent IgG.dgA immunotoxins. All three immunotoxins killed 50% of L540 cells at $0.9$–$2.0 \times 10^{-10}$M which is only 15–30 fold greater than is needed for an equivalent effect with ricin itself. HRS-1 which binds to the same epitope 11–23 fold more weakly was 40–90 times less active as an immunotoxin. Ki-1, which recognizes a different epitope and has a low affinity comparable to that of HRS-1, also yielded a relatively ineffective immunotoxin. Thus, it can be deduced that the affinity (avidity) of the CD30 antibodies rather than the epitope they recognize is the primary determinant of their potency as ricin A containing immunotoxins. Different conclusions about the importance of epitope location have been drawn from other studies. Shen et al. (43) concluded that both antibody affinity and epitope location determined the potency of CD22 immunotoxins. By contrast, Press et al. (44), in a study of three CD2 immunotoxins, concluded that epitope location critically influenced immunotoxin potency: immunotoxins recognizing one epitope on the CD2 molecule were rapidly transported to lysosomes and degraded, whereas an immunotoxin recognizing another epitope lying closer to the membrane remained in peripheral endocytic compartments and was powerfully toxic.

The Fab' fragments of HRS-3 and HRS-4 yielded immunotoxins that were only 7.8- and 3-fold less potent respectively than their IgG.dgA counterparts. Their lower activity can be explained by the fact that they can bind to only a single antigen on the cell surface and so bound 1.8–2.4 fold more weakly than their divalent counterparts. Fab' immunotoxins and IgG immunotoxins have different advantages that recommend their use for therapy. The stronger affinity, greater cytotoxic activity and longer half life in vivo are the major advantages of IgG immunotoxins over Fab' immunotoxins (43). The Fab' immunotoxins, on the other hand, may penetrate better into solid tumors (43) and have lower immunogenicity in man because they lack the relatively immunogenic Fc portion of the antibody (45).

EXAMPLE II

Antitumor Effects of Ricin A-Chain Immunotoxins Prepared from Intact Antibodies and Fab' Fragments on Solid Human Hodgkin's Disease Tumors in Mice I. Materials and Methods A. Materials Blue Sepharose CL-6B, Sepharose G25 (fine grade), Staphylococcal protein-A Sepharose, DEAE Sepharose and Sephacryl S-200 HR were obtained from Pharmacia Ltd. (Milton Keynes, England). Pepsin was purchased from Sigma (Poole, England). Tissue culture medium RPMI 1640 and fetal calf serum were from Gibco-Biocult Ltd. (Paisley, Scotland). Falcon tissue flasks were purchased from Becton Dickinson (Lincoln Park, USA). $^3$H-Leucine was obtained from Amersham International (Aylesbury, UK).

B. cells

The human Hodgkin's disease-derived cell line L540 (46) and the sublines which were obtained by reestablishing L540 tumors in culture were maintained in RPMI 1640 supplemented with 20% (v/v) fetal calf serum, 4 mM L-glutamine, 200 U/ml penicillin and 100 ug/ml streptomycin ('complete medium').

C. Antibodies

The mouse monoclonal antibodies used in this study were HRS-3, Ber-H2 (32), and IRac (47,48). All are of the IgGI subclass. HRS-3 and Ber-H2 recognize the CD30 antigen which has been shown to be composed of two nonreducible subunits of 105 and 120 kDa antigen on Hodgkin and Reed-Sternberg cells (47).

Ber-H2 and IRac were separated from the ascitic fluid of hybridoma-bearing BALB/c mice by affinity chromatography on Staphylococcal protein A-Sepharose. HRS-3 was purified by ammonium sulfate precipitation and ion exchange chromatography on DEAE-Sepharose.

The mouse IgG1 monoclonal antibody MRC OX7 which recognizes the mouse Thy 1.1 antigen (20) was used as a nonspecific control antibody.

All the antibodies were more than 90% pure when analyzed by SDS-PAGE using the Pharmacia pharmphast system.

D. Immunoperoxidase Staining of Human Tissues

Cryostat sections of normal human tissues were treated with antibodies and stained using indirect immunofluorescence and immunoperoxidase techniques as described elsewhere (65).

E. Crossblocking Experiments

Radioiodination and cross-blocking experiments were performed as described in Example I.

F. Preparation of Immunotoxins

Deglycosylated ricin A-chain immunotoxins were prepared essentially as described in Example I.

G. Cytotoxicity Assays

Cytotoxicity assays were performed essentially as described in Example I.

H. Mice

The mice used in the treatment experiments are N:NIH outbred stocks carrying a different combination of genes: the nude (nu) gene from N:NIH background, the xid from CBA/N and the beige (bg) gene from C 57 BL/6N. These so called 'triple beige' nudes (nu/nu/bg-xid) have a B-cell deficiency in addition to the NK and T cell defect known from beige nude mice (52).

Monogamous pairs of homologous males and heterozygous females for the nu gene were mated. The offspring were weaned after 21 days. Four to six week old homologous females weighing of 18-22 grams were used for the experiments.

I. Antitumor Experiments

For the establishment of solid tumors, $2.5 \times 10^7$ L540 cells in 200 ul complete medium were injected subcutaneously (s.c.) into the right posterior gluteal region of the triple beige mice. Tumors usually became visible after 5-7 days in more than 90% of the animals injected and grew to 1 cm diameter, corresponding to a volume of approximately 700 mm$^3$, within 30 days. Antitumor experiments were started when the tumors reached 60-80 mm$^3$, (approximately 0.5 cm diameter). Tumor diameters were recorded twice a week and the tumor volume was calculated as follows:

$$\text{volume} = d^2 \cdot D \cdot \frac{pi}{6}$$

Tumor bearing animals were randomly divided into groups of 8-10. Immunotoxins or antibodies were injected intravenously (i.v.) under sterile conditions into the tail vein in a volume of 200 ul PBS containing 2 mg/ml BSA. The doses of immunotoxins that were administered represented the same proportion of the $LD_{50}$ (about 40%) for both the intact antibody immunotoxins and the Fab' immunotoxins. The doses in terms of total protein were 48 ug for IgG immunotoxins and 206 ug for Fab' immunotoxins. This corresponds to 8 ug ricin A-chain for intact and 77.6 ug A-chain for Fab' immunotoxins. The doses of unconjugated antibodies or Fab' matched those of the immunotoxins: 40 ug for intact Abs and 129 ug for Fab' fragments.

The antitumor experiments were terminated 30 days after the animals were treated in order to keep tumor diameters less than 1.5 cm in accordance with British Home Office requirements. The antitumor effects of different treatments were compared by the 'growth index' which is calculated by dividing the mean tumor volume per group at day 30 by the mean tumor volume per group at the day of treatment (day 1). The statistical significance of the treatment results was calculated by the student's t test.

J. Establishment and Characterization of Recultures

Tumors were removed under sterile conditions, rinsed in complete medium and finely minced with a scalpel. Tumor cell-containing medium was then carefully transferred into 25 ml Falcon tissue flasks with a syringe, and incubated in complete medium. When the cultures appeared to be homogenous for L540 cells (about 2 weeks later) the cells were retreated with immunotoxins in vitro (see cytotoxicity assays). Sublines that were less susceptible to the immunotoxins were checked for changes of antigen expression by FACS analysis. The technique used for the FACS analyses has been described in Example I.

II. Results

A. Crossblocking of HRS-3, Ber-H2 and IRac

Figure 3:
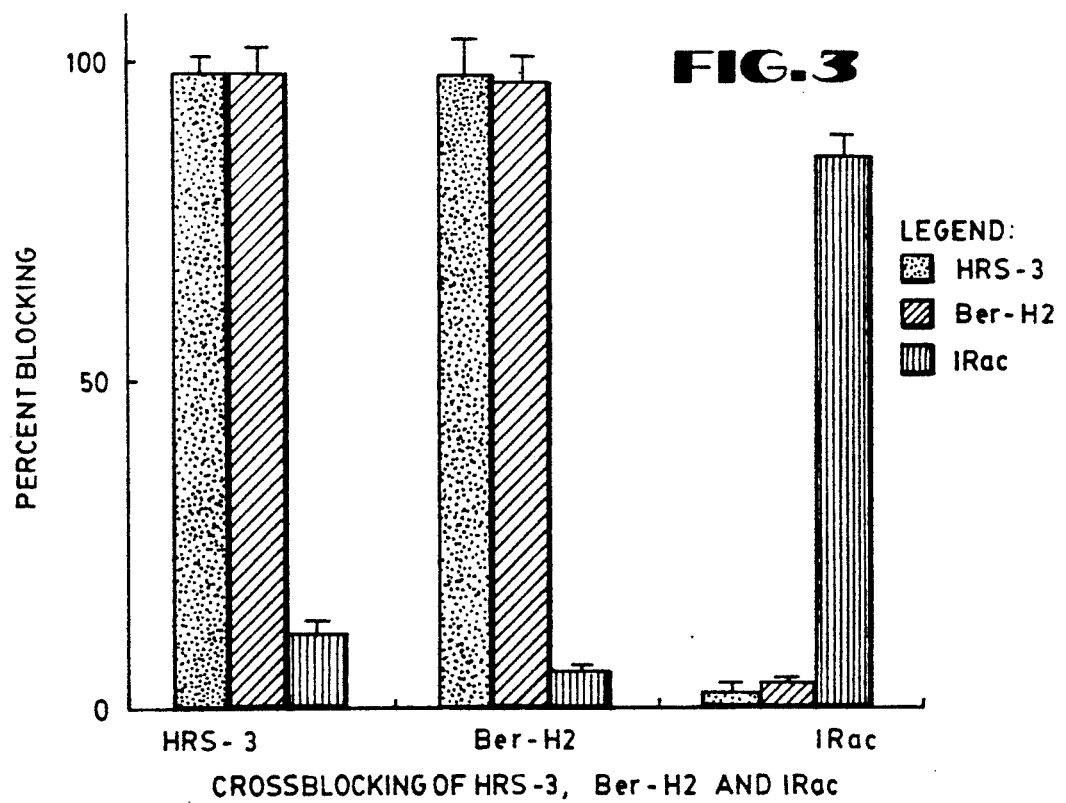
FIG. 3. $^{125}$I-labeled antibodies (0.5 ug) were mixed with a 100 fold excess (50 ug) of HRS-3° Ber-H2 and IRac and were added to L540 cells in PBS/BSA/N$_3$⁻ at 4° C. Each group histograms shows the percent of blocking of one of the $^{125}$I-labeled antibodies (marked with an asterisk) by the different unlabeled antibodies. The vertical lines on the histograms show the standard deviation of triplicate determinations.

Crossblocking experiments showed that neither HRS-3 nor Ber-H2 blocked the binding of IRac to L540 cells and vice versa. (FIG. 3). This is consistent with the finding that IRac recognizes a 70 kd Mr antigen on Hodgkin cells, whereas HRS-3 and Ber-H2 recognize the 105/120 kd Ki-1 (CD30) antigen. HRS-3 and Ber-H2 completely crossblocked each other's binding and seem therefore to recognize the same or at least two closely linked epitopes on the CD30 antigen, as also shown in Example I. The fact that IRac binds to a different antigen from HRS-3 and Ber-H2 indicates that IRac.dg and either HRS-3.dgA or Ber-H2.dgA may be useful as a 'cocktail' in vivo to maximize tumor cell kill.

B. Staining of Normal Human and Hodgkin's Disease Tissue

Immunoperoxidase staining of 28 different human tissues with HRS-3, Ber-H2 and IRac revealed no major cross-reactivity (Table VI). HRS-3 and Ber-H2 stained a few large lymphoid cells in the colon, lymph nodes, tonsils, and tissue of autoimmune thyroiditis. These cells were probably activated lymphocytes since CD30 is known to be expressed on such cells (26). IRac did not cross-react with any of the normal tissues tested as judged by the immunoperoxidase method.

All three antibodies strongly bound Hodgkin's disease derived cell lines. When tested on sections of Hodgkin's disease tissue from 30 patients, HRS-3 and Ber-H2 bound to more than 90% of the cases and stained >90% of those cells that could be morphologically identified as Hodgkin or Reed-Sternberg cells. By contrast, IRac preferentially stained nodular sclerosis and the mixed cellularity subtype and gave a more moderate labeling.

TABLE VI

Tissue Staining of Three Monoclonal Antibodies Recognizing HD/RS Cells

| Tissue | HRS-3 | Ber-H2 | IRac |
|---|---|---|---|
| Adrenal | − | − | − |
| Brain (cortex) | − | − | − |
| Brainstem | − | − | − |
| Breast | − | − | − |
| Cerebellum | − | − | − |
| Cervix | − | − | − |
| Colon | −* | −* | − |
| Gall bladder | − | − | − |
| Heart | − | − | − |
| Kidney | − | − | − |
| Liver | − | − | − |
| Lung | − | − | − |
| Lymph node | −* | −* | − |
| Mucosa (nasal) | − | − | − |
| Oesophagus | − | − | − |
| Ovary | − | − | − |
| Parathyroid | − | − | − |
| Prostate | − | − | − |
| Spleen | − | − | − |
| Stomach (antrum) | − | − | − |
| Stomach body | − | − | − |
| Testis | − | − | − |
| Thyroid | − | − | − |
| Thyroid (AI[1]) | −* | −* | − |
| Thyroid (Hashimoto's) | − | − | − |
| Tonsils | −* | −* | − |
| Uterus | − | − | − |
| Vagina | − | − | − |
| Hodgkin's disease[2] | +++ | +++ | (+++) |

[1]autoimmune Thyroiditis
[2]Primary material and cell lines
*rare cells within lymphoid tissue stain positively C. Cytotoxicity to L540 cells in vitro The most potent immunotoxin was that prepared from intact IRac antibody (Table VII). It had an $IC_{50}$ of $1 \times 10^{-11}$ M which is similar to ricin itself under the same experimental conditions. The next most potent immunotoxins were HRS-3.dgA and Ber-H2.dgA which were 9 times and 20 times less effective than IRac.dgA, with $IC_{50}$ values of $9 \times 10^{-11}$ and $2 \times 10^{-10}$ M respectively. The IRac Fab' immunotoxin ($IC_{50} = 6 \times 10$ M) was 60 fold less potent than the intact IRac.dgA immunotoxin whereas the HRS-3 Fab'.dgA ($IC_{50} = 7 \times 10^{-10}$) was only 7.8 times less potent than the intact HRS-3 immunotoxin.

The cytotoxic effect of all the immunotoxins was specific since the native antibodies and OX7.dgA, an immunotoxin that does not bind to L540 cells, were not toxic at $10^{-6}$ M.

TABLE VII

Cytotoxicity of Immunotoxins in vitro

| IMMUNOTOXIN | $IC_{50}$ (M)[1] |
|---|---|
| Ber-H2.dgA | $2.0 \pm 0.5 \times 10^{-10}$ |
| HRS-3.dgA | $9.0 \pm 0.8 \times 10^{-11}$ |
| HRS-3Fab'dgA | $7.0 \pm 1.5 \times 10^{-10}$ |
| IRac.dgA | $1.0 \pm 0.2 \times 10^{-11}$ |
| IRacFab'.dgA | $6.0 \pm 1.2 \times 10^{-10}$ |

[1]Average of at least 3 separate experiments ± standard deviation

D. Antitumor Effects on Solid L540 Tumors in vivo
1Intact Antibody Immunotoxins

In Table VIII are listed the detailed results of a series of antitumor experiments in which HRS-3, Ber-H2 and IRac immunotoxins were administered at various doses to triple beige nude mice bearing solid L540 tumors of various dimensions. FIG. 4a shows a typical experiment in which intact antibody immunotoxins were administered to mice with tumors of 60–80 mm³ (0.5 cm diameter). All three immunotoxins had impressive antitumor activity. IRac.dgA was the most powerful (growth index 0.8), followed by HRS-3.dgA (growth index 1.4) and then BerH2.dgA (growth index 4.6). The difference in antitumor activity between IRac.dgA and HRS-3.dgA did not reach statistical significance whereas the difference between IRac.dgA and Ber-H2.dgA was statistically significant (P<0.02). There were several complete remissions: 17/24 for IRac.dgA, 11/16 for HRS-3.dgA and 3/8 for Ber-H2.dgA. Of these, five IRac.dgA- and four HRS-3.dgA-treated animals had relapses after 5-15 days. No relapses were observed after 20 days of complete remission. In contrast, the tumors grew progressively in untreated animals (growth index 9.7) and in animals treated with an immunotoxin of irrelevant specificity, OX7.dgA (growth index 8.7).

It is possible that part of the antitumor activity of the immunotoxins was mediated through the antibody component alone, since the native antibodies, when administered at doses equivalent to those in the immunotoxins, appeared slightly to retard tumor growth. The growth indices were 7.5 for HRS-3, 8.8 for Ber-H2 and 7.5 for IRac as compared with 9.7 for the untreated control group. None of these differences was, however, statistically significant. In each group of eight mice treated with the antibodies there was one lasting complete remission.

TABLE VIII

Treatment of Solids L540 Tumors with Different Immunotoxins in Triple Beign Mice

| Treatment | Dose (ug Protein) | Average tumor size (mm3) | | Growth index 1) (day 30/day 1) | Number of mice treated | Response | | |
|---|---|---|---|---|---|---|---|---|
| | | Day 1 | Day 30 | | | CR | Relapse | PR or NR |
| PBS | — | 69 | 667 | 9.7 ± 1.6 | 24 2) | 1 | — | 23 |
| PBS | — | 306 | 1854 | 5.8 ± 0.7 | 8 | — | — | 8 |
| IRac.dgA | 48 | 15 | 0 | 0.0 ± 0.0 | 10 10 | — | — | |
| IRac.dgA | 48 | 79 | 65 | 0.8 ± 0.2 | 24 2) | 12 | 5 | 7 |
| IRac.dgA | 48 | 407 | 360 | 0.9 ± 0.4 | 8 | 1 | 2 | 5 |
| IRac | 40 | 54 | 407 | 7.5 ± 1.5 | 8 | 1 | — | 7 |
| IRacFab'.dgA | 206 | 53 | 422 | 8.0 ± 2.9 | 8 | 2 | — | 6 |
| IRacFab' | 129 | 75 | 796 | 10.6 ± 1.9 | 8 | — | — | 8 |
| HRS-3.dgA | 48 | 99 | 134 | 1.4 ± 0.5 | 16 3) | 7 | 4 | 5 |
| HRS-3 | 40 | 62 | 464 | 7.5 ± 1.8 | 8 | 1 | 1 | 6 |
| HRS-3Fab'dgA | 206 | 70 | 189 | 2.7 ± 0.7 | 8 | 2 | 3 | 3 |

TABLE VIII-continued

Treatment of Solids L540 Tumors with Different Immunotoxins in Triple Beign Mice

| Treatment | Dose (ug Protein) | Average tumor size (mm3) | | Growth index 1) (day 30/day 1) | Number of mice treated | Response | | |
|---|---|---|---|---|---|---|---|---|
| | | Day 1 | Day 30 | | | CR | Relapse | PR or NR |
| HRS-3Fab' | 129 | 82 | 651 | 7.9 ± 1.5 | 8 | — | — | 8 |
| Ber-H2.dgA | 48 | 63 | 291 | 4.6 ± 1.8 | 8 | 3 | — | 5 |
| Ber-H2 | 40 | 61 | 529 | 8.8 ± 1.7 | 8 | 1 | — | 7 |
| OX7.dgA | 48 | 68 | 589 | 8.7 ± 1.1 | 8 | — | — | 8 |

1) arithmetic mean ± one standard error (s.e.)
2) average of 3 separate experiments
3) average of 2 separate experiments
CR = complete remission
PR = partial remission
NR = no response 2. Fab' Immunotoxins The Fab' immunotoxins were administered to the mice in doses that represented the same proportion of the $LD_{50}$ (i.e., 40%) as for the intact antibody immunotoxins. The HRS-3 Fab' immunotoxin was only slightly less effective at inhibiting the growth of 60–80 $mm^3$ (0.5 cm diameter) tumors than was the intact HRS-3 immunotoxin (Table VIII and FIG. 4c). The tumor index was 2.7 in the HRS-3 Fab'.dgA recipients as compared with 1.4 in the recipients of the corresponding intact antibody immunotoxins. This difference is not statistically significant ($P > 0.05$). The overall number of complete remissions was similar (5/8 for HRS-3 Fab'.-dgA versus 11/16 for HRS-3.dgA, respectively), but there was a higher proportion of relapses in the HRS-3 Fab'.dgA treated group (3/8 versus 4/16 respectively).

In contrast, the IRac Fab' immunotoxin was substantially ($P < 0.002$) less effective than its intact antibody counterpart (growth index: 8.0 versus 0.8; permanent CR: 2/8 versus 12/24).

The Fab' fragments of HRS-3 and IRac alone had no antitumor effect (FIG. 4d).

E . Dependence of the Antitumor Effect on Tumor Size at the Time of Treatment

To evaluate the effect of tumor size on the responsiveness to the treatment, the effects of IRac.dgA on the rate of tumor growth in groups of mice with small tumors (10–20 $mm^3$; approx. 2 mm in diameter) when compared with groups with large tumors (400–600 $mm^3$; approximately 1 cm in diameter) (see FIG. 5). All animals with small tumors had lasting complete remissions. By contrast, only 3/8 animals with large tumors had complete remissions and, of these, 2 animals subsequently relapsed.

F Emergence of Immunotoxin-Resistant Tumor Mutants in vivo

Tumors from mice which had complete remissions after treatment with HRS-3.dgA or IRac.dgA but which subsequently relapsed were re-established in tissue culture and their immunotoxin-sensitivity was determined. All four sublines established from relapsed HRS-3.dgA recipients were as sensitive as the original L540 line to HRS-3.dgA and IRac.dgA. By contrast, three of four sublines that originated from relapsed IRac.dgA recipients were 40, 60 and 200 times less sensitive to IRac.dgA than the original L540 line (Table IX). The degree of resistance of the sublines to IRac.-dgA correlated with the decrease in their ability to bind IRac antibody as measured by FACS analyses. The mean fluorescence intensity (MFI) of the sublines was 13%, 24% and 33% of the MFI of the parental L540 line.

These results indicate that the L540 tumor originally implanted into the mice contained a few IRac antigen-deficient mutants which were not killed by IRac.dgA and which after a period of complete remission regrew into solid tumors at the original tumor site. Importantly, the IRac.dgA-resistant sublines were approximately as sensitive to HRS-3.dgA as the original L540 line indicating that treatment of the mice with a cocktail of IRac.dgA and HRS-3.dgA would reduce the likelihood of mutant tumor cell escape.

TABLE IX

Characteristics of L540 Sublines Derived from IRac.dgA-treated Mice which had Complete Remissions but Subsequently Relapsed

| Subline | Resistant or sensitive | Antigen density (% MFI[1]) | Immunotoxin sensitivity $IC_{50}$ (M) | |
|---|---|---|---|---|
| | | | IRac.dgA | HRS-3.dgA |
| 1 | Sensitive | 87 | $2 \times 10^{-11}$ | $1 \times 10^{-10}$ |
| 2 | Resistant | 33 | $4 \times 10^{-10}$ | $6 \times 10^{-11}$ |
| 3 | Resistant | 24 | $6 \times 10^{-10}$ | $1 \times 10^{-10}$ |
| 4 | Resistant | 13 | $2 \times 10^{-9}$ | $4 \times 10^{-10}$ |
| L540 | Sensitive | 100 | $1 \times 10^{-11}$ | $9 \times 10^{-11}$ |

[1]MFI of the sublines expressed as percentage of the MFI of original L540 cells stained with IRac at saturating concentrations In a further study, tumors from mice which showed relatively little response (i.e., did not reach CR) after IRac.dgA or HRS-3.dgA therapy were re-established in tissue culture and their immunotoxin sensitivity was determined. All three sublines derived from HRS-3.dgA recipients and both sublines derived from IRac.-dgA recipients were as sensitive to immunotoxins as the original L540 line. Thus, the relatively poor responsiveness of these tumors to immunotoxin therapy was not because the tumor cells themselves were resistant to the immunotoxins.

III. DISCUSSION OF EXAMPLE II STUDIES

The major findings to emerge from this study were: i) a single intravenous injection of the intact immunotoxins, HRS-3.dgA or IRac.dgA, cured up to 44–50% of mice with solid Hodgkin tumors of 60–80 $mm^3$ size; ii) the HRS-3 Fab' immunotoxin was slightly less potent in vitro and in vivo than the intact HRS-3 immunotoxin, whereas the IRac Fab' immunotoxin was much less potent compared with the intact IRac immunotoxin; iii) tumors that regrew after IRac.dgA treatment in mice consisted mainly of mutants with a reduced sensitivity to IRac.dgA but not to HRS-L 3.dgA; iv) since HRS-3.dgA (or HRS-3 Fab'.dgA) and IRac.dgA combine highly specific cytotoxicity in vitro, potent antitumor effects in vivo, little cross-reactivity with normal human tissue and recognize different antigens, they could be used as a cocktail for the treatment of patients with Hodgkin's disease.

The immunotoxins used in this example exhibited surprisingly good antitumor effects in a solid Hodgkin's disease xenograft model. The growth index (ratio of tumor volume per group on day 30:day 1) was 0.8 for IRac.dgA, 1.4 for HRS-3.dgA and 4.6 for Ber-H2.dgA as compared with 9.7 for untreated control animals. With IRac.dgA recipients, tumors of approximately 1 cm diameter were smaller on average 30 days after treatment than on the day of treatment. In addition, 100% of small (10-20 mm$^3$) tumors were destroyed by a single IRac.dgA injection, indicating the importance of tumor size on complete remission rates. Possible explanations for the high in vivo efficacy of the present immunotoxins are that deglycosylated ricin A-chain, the SMPT linker, and a final purification step on Blue Sepharose were employed when manufacturing the immunotoxin. These procedures enable the preparation of 'second generation' immunotoxins that have higher purity, higher in vivo stability, and which avoid liver entrapment better than immunotoxins of the first generation, resulting in substantially improved antitumor activity in mouse tumor models.

The intact HRS-3 and IRac immunotoxins had superior antitumor effects to their Fab' counterparts. With the HRS-3 immunotoxins the differences were small: HRS-3.dgA treatment resulted in lasting complete remissions in 7/16 mice and a tumor growth index of 1.4 as compared with 2/8 mice and a tumor growth index of 2.7 in the recipients of HRS-3 Fab'.dgA. These differences were more marked with the IRac immunotoxins; treatment with IRac.dgA produced lasting complete remissions in 12/24 mice and a growth index of 0.8 as compared with 2/8 mice and a growth index of 8.0 in the recipients of IRac Fab'.dgA. The difference in the degree of superiority of the two intact antibody immunotoxins over their Fab' counterparts correlated with their relative cytotoxic potency in vitro. The HRS-3 Fab'.dgA was only 7.8 fold less potent at killing L540 cells in vitro than the intact antibody immunotoxin, whereas the IRac Fab'.dgA was 60-fold less potent. The higher cytotoxicity of IgG over Fab' immunotoxins in vitro is well established and due to the superior affinity of the bivalent intact immunotoxin.

Several tumors that resisted immunotoxin treatment or which responded but subsequently regrew were reestablished in vitro and their sensitivity to immunotoxins was determined. The 5 sublines established from tumors that were resistant to HRS-3.dgA in mice were as sensitive to the immunotoxins as the original L540 line in vitro, suggesting that the amount of immunotoxin that reached the solid tumor was not sufficient to kill all sensitivity tumor cells.

By contrast, three of four tumors that relapsed after IRac.dgA treatment were 40, 60 and 200 times less sensitive to IRac.dgA in vitro than the original L540 cells. The three tumors all had a reduced expression of the IRac antigen suggesting that the immunotoxin killed the majority of cells in the tumor with normal levels of antigen, leaving a few antigen-deficient mutants that later regrew into sizeable tumors. Importantly, the sublines were still sensitive to HRS-3.dgA. This strongly suggests that the problem of antigenic heterogeneity can be overcome, at least in part, by the administration of immunotoxin cocktails.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

1. De Vita, et al. (1967), A combination chemotherapy in the treatment of advanced Hodgkin's disease. *Proc. Am. Assoc. Cancer Res.*, 8:13a.
2. Bonadonna et al. (1982), ABVD chemotherapy in the treatment of Hodgkin's disease. *Cancer Treat. Rev.*, 9:21-35.
3. De Vita (1981), The consequences of the chemotherapy of Hodgkin's disease: The 10th David A. Karnofsky Memorial Lecture. *Cancer*, 47: 1-13.
4. Longo et al. (1986), Twenty years of MOPP therapy for Hodgkin's disease. *J. Clin. Oncol.*, 4:1295-1306.
5. Valagussa et al. (1986), Second acute leukemia and other malignancies following treatment for Hodgkin's disease. *J. Clin. Oncol.*, 4:830-837.
6. Santoro et al. (1986) CCNU, Etoposide and Prednimustine (CEP) in refractory Hodgkin's disease. *Semin. Oncol.*, 13, suppl. 1:23.
7. Hagemeister et al. (1987), MIME chemotherapy (Methyl-GAG, Ifosfamide, Methodtrexate, Etoposide) as treatment for recurrent Hodgkin's disease. *J. Clin. Oncol.*, 5:556-561.
8. Pfrendschuh et al. (1987), Lomustine, Etoposide, Vindesine, and Dexamethasone (CEVD) in Hodgkin's lymphoma refractory to Cyclophosphamide, Vincristine, Procarbazine, and Prednisone (COPP) and Doxorubicin, Bleomycin, Vinblastine, and Decarbazine (ABVD)L: A multicenter trial of the Germany Hodgkin Study Group. *Cancer Treatment Reports*, 71:1203-1207.
9. Zulian et al. (1989), High dose melphalan, BCNU and Etoposide with autologous bone marrow transplantation for Hodgkin's disease. *Br. J. Cancer*, 59:631-635.
10. Gribben et al., (1989), Successful treatment of refractory Hodgkin's disease by high-dose combination chemotherapy and autologous bone marrow transplantation *Blood*, 73:340-344.
11. Valagussa et al., (1986), Second acute leukemia and other malignancies following treatment for Hodgkin's disease. *J. Clin. Oncol.*, 4:830-837.
12. Blakey et al. (1988), Antibody Toxin Conjugates: A perspective. Waldmann H (ed): Monoclonal Antibody Therapy. *Prog Allergy. Basel, Karger*, 45:50-90.
13. Vitetta et al., (1987), Redesigning nature's poisons to create anti-tumor reagents. *Science*, 238:1098.
14. Spitler et al. (1987), Therapy of patients with malignant melanoma using a monoclonal antimelanoma antibody-ricin A-chain immunotoxin. *Cancer Res.*, 47:1717-1723.
15. Laurent et al. (1986), Effects of therapy with T101 ricin A-chain immunotoxin in two leukemia patients. *Blood*, 67:1680-1687.

16. Byers et al. (1987), A phase I study using pan T-lymphocyte-ricin-A-chain immunotoxin to treat graft versus host disease; in Royston, Dillman, Second International Conference on Monoclonal Antibody Immunoconjugates for Cancer (UCSD Cancer Center, San Diego).
17. Bernhard et al. (1983), Guinea pig line 10 hepatocarcinoma model: characterization of monoclonal antibody and in vivo effect of unconjugated antibody and antibody conjugated to diphtheria toxin A-chain. *Cancer Res.*, 43:4420–4428.
18. Hwang et al., (1984), Selective antitumor effect on L10 Hepatocarcinoma cells of a potent immunoconjugate composed of the A chain on Abrin and a monoclonal antibody to a hepatoma-associated antigen. *Cancer Res.*, 44:4578–4586.
19. Leonhard et al., (1988), Inhibition of human T-cell tumor growth by T101-ricin A-chain in an athymic mouse model. *Cancer Res.*, 48:4862–4867.
20. Roth et al., (1988), Mediation of reduction of spontaneous and experimental pulmonary metastases by ricin A-chain immunotoxin 45-2D9-RTA with potentiation by systemic monesin in mice. *Cancer Res.*, 48:3496–3501.
21. Byers et al., (1987), Inhibition of growth of human tumor xenografts in athymic mice treated with ricin toxin A chain-monoclonal antibody 791T/36 conjugates. *Cancer Res.*, 47:5042–5046.
22. Hara et al., (1988), Efficient transplantation of human non-T-leukemia cells into nude mice and induction of complete regression of the transplanted distinct tumors by ricin A-chain conjugates of monoclonal antibodies SN5 and SN6. *Cancer Res.*, 48:4673–4680.
23. Schwab et al., (1982), Production of a Monoclonal antibody specific for Hodgkin and Sternberg-Reed cells of Hodgkin's disease and a subset of normal lymphoid cells. *Nature*, 299:65–67.
24. Froese et al., (1987), Biochemical characterization and biosynthesis of the Ki-1 antigen in Hodgkin-derived and virus-transformed human B and T lymphoid cell lines. *J. of Immunology*, 139:2081–2087.
25. Schaadt et al., (1980), Two neoplastic cell lines with unique features derived from Hodgkin's disease. *Int. J. Cancer*, 26:723–731.
26. Stein et al., (1985), The expression of the Hodgkin's disease associated antigen Ki-1 in reactive and neoplastic lymphoid tissue: Evidence that Sternberg-Reed cells and histiocytic malignancies are derived from activated lymphoid cells. *Blood*, 66:848–858.
27. Ralfkiaer et al. (1987), Expression of a Hodgkin and Reed-Sternberg cell associated antigen (Ki-1) in cutaneous lymphoid infiltrates. *Arch. Dermatol. Res.*, 279:285–292.
28. Pallesen et al. (1988), Ki-1 (CD30) antigen is regularly expressed by tumor cells of embryonal carcinoma. *Am. J. Pathol.*, 133:446–450.
29. Fulton et al., (1986), Purification of ricin A1, A2 and B chains and characterization of their cytotoxicity. *J. Biol. Chem.*, 261:5314–5319.
30. Thorpe et al., (1985), Modification of the carbohydrate in ricin with metaperiodate-cyanoborohydride mixtures. Effect on toxicity and in vivo distribution. *Eur. J. Biochem.*, 147:197–206.
31. Pfeundschuh et al. (1988), Hodgkin and Reed-Sternberg cell associated monoclonal antibodies HSR-1 and HSR-2 react with activated cells of lymphoid and monocytoid origin. *Anticancer Res.*, 8:217–224.
32. Schwarting et al. (1987), Ber-H2: a new monoclonal antibody of the Ki-1 family for the detection of Hodgkin's disease in formaldehyde-fixed tissue sections. In: A. J. McMichael (ed.), Leukocyte Typing III, pp. 574–575, Oxford University Press.
33. Mason et al. (1980), The kinetics of antibody binding to membrane antigens in solution and at the cell surface. *Biochem. J.*, 187:1–20.
34. Thorpe et al. (1987), New coupling agents for the synthesis of immunotoxins containing a hindered disulfide bond with improved stability in vivo. *Cancer Res.*, 47:5924–5931.
35. Ghetie et al. (1988), "Evaluation of Ricin A-chain immunotoxins directed against CD19 and CD22 antigens on normal and malignant human B-cells as potential reagents for in vivo therapy", *Cancer Res.*, 48:2610–2617.
36. Allen et al. (1962), Synthesis of hemoglobin in a cell-free system. *J. Biol. Chem.*, 237:760–767.
37. Fraker et al. (1978), Protein and cell membrane iodination with a sparingly soluble chloramide, 1,3,4,6-tetrachloro-3alpha, 6 alpha diphenylglycouril. *Biophys. Biochem. Res. Commun.*, 80:849.
38. Scatchard, G. (1949), The attraction of proteins for small molecules and ions. *Ann. N.Y. Acad. Sci.*, 51:660–672.
39. Hsu et al. (1981), Use of Avidin-biotin-peroxidase complex (ABC) in immunoperoxidase techniques: a comparison between ABC and unlabeled antibody (PAP) procedures. *Histochem. Cytochem.*, 29:577–580.
40. Masuho et al. (1982), Importance of the antigen-binding valency and the nature of the cross-linking bond in ricin A-chain conjugates with antibody. *J. Biochem.*, 91:1583–1591.
41. Fulton et al. (1986), The effect of antibody valency and lysosomotropic amines on the synergy between ricin A-chain-and B chain-containing immunotoxins. *J. Immunol.*, 136:3103–3109.
42. Li et al. (1989), The epitope specificity and tissue reactivity of four murine monoclonal anti-CD22 antibodies. *Cell. Immunol.*, 118:85–99.
43. Stein et al., (1982), Identification of Hodgkin and Reed-Sternberg cells as a unique cell type derived from newly detected small cell population. *Int. J. Cancer*, 30:445–459.
44. Press et al. (1988), Ricin A-chain containing immunotoxins directed against different epitopes on the CD2 molecule differ in their ability to kill normal and malignant T cells. *J. Immunology*, 141:4410–4417.
45. Smith et al. (1979), Immunogenicity and kinetics of distribution and elimination of sheep digoxin-specific IgG and Fab fragments in the rabbit and baboon. *Clin. Exp. Immunol.*, 36:384–396.
46. Schaadt et al. (1980), Two neoplastic cell lines with unique features derived from Hodgkin's disease. *Int. J. Cancer*, 26:723–731.
47. Hsu et al. (1987), Effect of monoclonal antibodies anti-2H9, anti-IRac, and anti-HeFi-1 on the surface antigens of Reed-Sternberg cells. *J. Nat. Cancer Inst.*, 5:1091–1097.
48. Hsu et al. (1986), Expression on an activated interdigitating reticulum cell antigen (IRac) in Reed-Sternberg cells. *Lab. Invest.*, 54:27A.
49. Froese et al. (1987), Biochemical characterization and biosynthesis of the Ki-1 antigen in Hodgkin-derived and virus-transformed human B and T lymphoid cell lines. *J. of Immunol.*, 139:2081–2087.

50. Mason et al. (1980), The kinetics of antibody binding to membrane antigens in solution and at the cell surface. *Biochem. J.*, 187:1–20.
51. Ghetie et al. (1988), Evaluation of Ricin A-chain immunotoxins directed against CD19 and CD22 antigens on normal and malignant human B-cells as potential reagents for in vivo therapy. *Cancer Res.*, 48:2610–1617.
52. Pflumio et al. (1989), The C57BL/6 nude, beige mouse: A model of combined T cell and NK effector cell immunodeficiency. *Cellular Immunology*, 120:218–229.
53. Murray et al. (1984), *N. Engl. J. Med.*, 310:883.
54. Wawrzynczak et al. (1987), In Immunoconjugates: Antibody Conjugates in Radioimagery and Therapy of Cancer, ed. C. W. Vogel, Oxford U. Press, pp. 28–55; U.S. Ser. No. 07/090,386, filed Aug. 27, 1987.
55. Funmatsu et al. (1970), *Jap. J. Med. Sci. Biol.*, 23:264–267.
56. Fulton et al. (1988), *Cancer Res.*, 48:2618–2625.
57. O'Hare et al. (1987), *FEBS Lett.*, 216:731.
58. Vitetta (1988), *J. Immunol.*, 136:1880–1887.
59. Kearney et al. (1979), *J. Immunol.*, 123:1548–1550.
60. Hsu et al. (1987), Effect of monoclonal antibodies anti-2H9, anti-IRac, and anti-HeFi-1 on the surface antigen of Reed-Sternberg cells. *J. Natl. Cancer Inst.*, 79:1091–1099.
61. Hecht et al. (1985), "Production and characterization of a monoclonal antibody that binds Reed-Sternberg cells", *J. Immunol.*, 143:4231–4236.
62. Hsu et al. (1986), "Monoclonal antibodies against SU-DHL-1 cells stain the neoplastic cells in true histiocytic lymphoma, malignant histiocytosis, and Hodgkin's disease", *Blood*, 68:213–219.
63. Hsu et al. (1982), "Color modification of diaminobenzidine (DAB) precipitation by metallic ions and its application for double immunohistochemistry", *J. Histochem. Cytochem.*, 30:1079–1082.
64. O'Hare et al. (1987), *FEBS Lett.*, 216:731; Lamb et al. (1985), *Eur. J. Biochem.*, 148:265–270; Halling et al. (1985), *Nucl. Acids. Res.*, 13:8019–8033.
65. Janossy et al. (1987), 'Immunofluorescence and immunohistology in lymphomas'; a practical approach, (ed. G. G. B. Keans), IRL Press, Oxford, pp. 67–108,
66. Kamesaki et al. (1986), Cytochemical, immunologic, chromosomal, & molecular genetic analysis of a novel cell line derived from Hodgkin's Disease Blood, 68:285–292.
67. Hsu et al. (1988), Reed-Sternberg cells in Hodgkin's cell lines HDLM, L-428 and KM-H2 are not actively replicating: lack of bromodeoxyuridine uptake by multi-nuclear cells in culture, *Blood*, 71:1382–1389.
68. Poppema et al. (1985), Morphdogic, immunologic, enzyme, histochemical and chromosomal analysis of a cell line derived from Hodgkin's Disease. *Cancer*, 55:683.
69. Knowles et al. (1987), *Anal. Biochem.*, 120:440–443; U.S. Ser. No. 07/150,190, filed Jan. 29, 1988.
70. *Remington's Pharmaceutical Sciences*, 16th edition, (1980), Mack Publishing Company, edited by Oslo et al.
71. Schaadt et al. (1980), *Int. J. Cancer*, 26:723–731.
72. Diehl et al. (1981), *J. Cancer Res. Clin. Oncol.*, 101:111–124.
73. Murphy et al. (1986), *Proc. Natl. Acad. Sci. U.S.A.*, 83:8258.
74. Johnson et al. (1988), *Jrnl. Biol. Chem.*, 63:1295.
75. Thorpe et al. (1984), *Eur. J. Biochem.*, 140:63–71.
76. Breitmeyer et al. (1989), "Blocked ricin immunotoxin therapy of malignant lymphoma", in *Monoclonal Antibody Immunoconjugates in Cancer Therapy*, Chicago, p. 28.

What is claimed is:

1. An immunotoxin conjugate comprising:
   (a) a cell surface binding ligand comprised of an antibody, or antibody fragment derived from such an antibody, said antibody having a binding affinity Kd of less than about 200 nM for L540 Hodgkin cells and capable of at least about 70% cross-blocking of HRS-3 or IRac binding to L540 Hodgkin cells when present at about a 100-fold excess with respect to said HRS-3 or IRac; and
   (b) a toxin moiety conjugated to said binding ligand by means of a disulfide linkage;
   wherein the conjugate exhibits an IC$_{50}$ of less than about $10^{-9}$M on L540 Hodgkin cells.

2. The conjugate of claim 1 wherein said binding ligand exhibits Kd of less than about 40 nM for L540 Hodgkin cells.

3. The conjugate of claim 2, wherein said binding ligand exhibits a Kd of less than about 20 nM for L540 Hodgkin cells.

4. The conjugate of claim 1, wherein said binding ligand exhibits a Kd of between about 7 and about 27 nM for L540 Hodgkin cells.

5. The conjugate of claim 1, wherein about $3 \times 10^{-6}$ molecules of said binding ligand will bind per L540 Hodgkin cell at saturation.

6. The conjugate of claim 1, further defined as exhibiting an IC$_{50}$ of less than or equal to about $10^{-10}$M on L540 Hodgkin cells.

7. The conjugate of claim 1, further defined as exhibiting an IC$_{50}$ of between about $7 \times 10^{-10}$ and about $1 \times 10^{-11}$M on L540 Hodgkin cells.

8. The conjugate of claim 1, wherein said binding ligand is defined as one capable of at least about 90% cross-blocking of HRS-3.

9. The conjugate of claim 1, wherein said binding ligand is defined as one capable of at least about 90% cross-blocking of IRac binding.

10. The conjugate of claim 1, wherein said binding ligand is defined as one essentially free of binding affinity for normal tissues.

11. The conjugate of claim 1, wherein the toxin moiety comprises an A chain toxin, ribosome inactivating toxin or Pseudomonas exotoxin.

12. The conjugate of claim 11, wherein the toxin moiety comprises ricin A chain.

13. The conjugate of claim 11, wherein the toxin moiety comprises deglycosylated ricin A chain.

14. The conjugate of claim 1, wherein the binding ligand is conjugated to the toxin moiety by means of a linker comprising a disulfide bond.

15. The conjugate of claim 14, wherein the linker comprises a hindered disulfide bond.

16. The conjugate of claim 15, wherein the linker comprises an SMPT or SPDB linker.

17. The conjugate of claim 1, wherein the binding ligand comprises an IgG molecule.

18. The conjugate of claim 1, wherein the binding ligand comprises an Fab' fragment.

19. The conjugate of claim 1, wherein the conjugate is further defined as HRS-3.dgA.

20. The conjugate of claim 1, wherein the conjugate is further defined as IRac.dgA.

21. The conjugate of claim 1, wherein the conjugate is further defined as HRS-3Fab'.dgA.

22. The conjugate of claim 1, wherein the conjugate is further defined as IRacFab'.dgA.

23. A method for killing Hodgkin's disease cells comprising subjecting said cells to an amount of an immunotoxin conjugate in accordance with claim 1 that is effective to kill said cells.

24. A therapeutic composition comprising a therapeutically effective amount of an immunotoxin conjugate in accordance with claim 1, dispersed in a pharmacologically acceptable diluent.

25. The conjugate of claim 24 comprising a therapeutically effective amount of a first and a second immunotoxin composition, the first and second immunotoxin conjugate having binding affinity for immunologically distinct epitopes.

26. The composition of claim 25 wherein the immunologically distinct epitopes reside on different antigens.

27. The composition of claim 25 wherein said first immunotoxin conjugate has binding affinity for an epitope on CD30 antigen and said second immunotoxin conjugate has binding affinity for an epitope on 70 kDa antigen recognized by IRac.

28. The composition of claim 27 wherein said first immunotoxin conjugate comprises the conjugate of claim 19 or 21, and said second, immunotoxin conjugate comprises the conjugate of claim 20 or 22.

29. A method for the treatment of Hodgkin's disease comprising administering to a patient in need of such treatment an amount of therapeutic composition in accordance with claim 24 that is effective to kill Hodgkin disease cells in the patient.

* * * * *

UNITED STATES PATENT AND TRADEMARK OFFICE
CERTIFICATE OF CORRECTION

PATENT NO. : 5,165,923
DATED : November 24, 1992
INVENTOR(S) : Thorpe, et al

It is certified that error appears in the above-indentified patent and that said Letters Patent is hereby corrected as shown below:

In claim 2, line 19, column 38, insert a --","-- (comma) after "1" --.

In claim 25, line 14, column 39, delete "conjugate" and insert with -- "composition" --.

In claim 25, line 16, column 39, replace "composition" with --conjugate"--.

Signed and Sealed this

Twenty-sixth Day of October, 1993

Attest:

BRUCE LEHMAN

*Attesting Officer*   *Commissioner of Patents and Trademarks*